(12) United States Patent
Glossop et al.

(10) Patent No.: US 8,822,439 B2
(45) Date of Patent: Sep. 2, 2014

(54) GLUCOCORTICOID RECEPTOR AGONISTS

(75) Inventors: Paul Alan Glossop, Sandwich (GB);
David Simon Millan, Sandwich (GB);
David Anthony Price, Mystic, CT (US)

(73) Assignee: Pfizer Inc., New York, NY (US)

( * ) Notice: Subject to any disclaimer, the term of this patent is extended or adjusted under 35 U.S.C. 154(b) by 710 days.

(21) Appl. No.: 12/276,925

(22) Filed: Nov. 24, 2008

(65) Prior Publication Data
US 2009/0227548 A1 Sep. 10, 2009

Related U.S. Application Data

(60) Provisional application No. 60/991,354, filed on Nov. 30, 2007, provisional application No. 61/057,241, filed on May 30, 2008, provisional application No. 61/079,555, filed on Jul. 10, 2008.

(51) Int. Cl.
*A61K 31/58* (2006.01)
*C07J 71/00* (2006.01)

(52) U.S. Cl.
USPC .............................. 514/171; 514/174; 540/66

(58) Field of Classification Search
USPC ..................................... 514/174, 171; 540/66
See application file for complete search history.

(56) References Cited

U.S. PATENT DOCUMENTS 3,197,469 A 7/1965 Fried et al. ............... 260/239.55

FOREIGN PATENT DOCUMENTS

| WO | WO 2004037197 | 5/2004 | |
|----|----|----|----|
| WO | WO 2005028495 | 3/2005 | ............... C07J 71/00 |
| WO | WO 2005044759 | 5/2005 | |
| WO | WO 2005074924 | 8/2005 | ........... A61K 31/428 |
| WO | WO 2005099720 | 10/2005 | ........... A61K 31/704 |

OTHER PUBLICATIONS

Ravikuma et al., Tetrahedron Letters, vol. 39, No. 20, pp. 3141-3144, 1998.

*Primary Examiner* — Sabiha N Qazi

(57) ABSTRACT

This invention relates to novel glucocorticoid receptor agonists of formula (I):

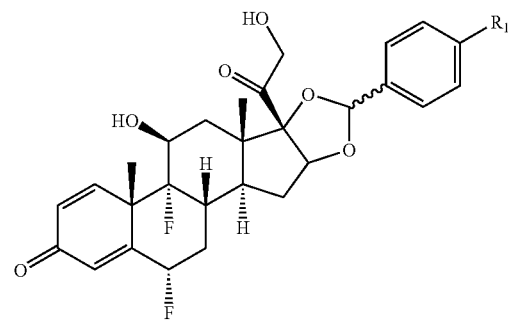

Figure 1:
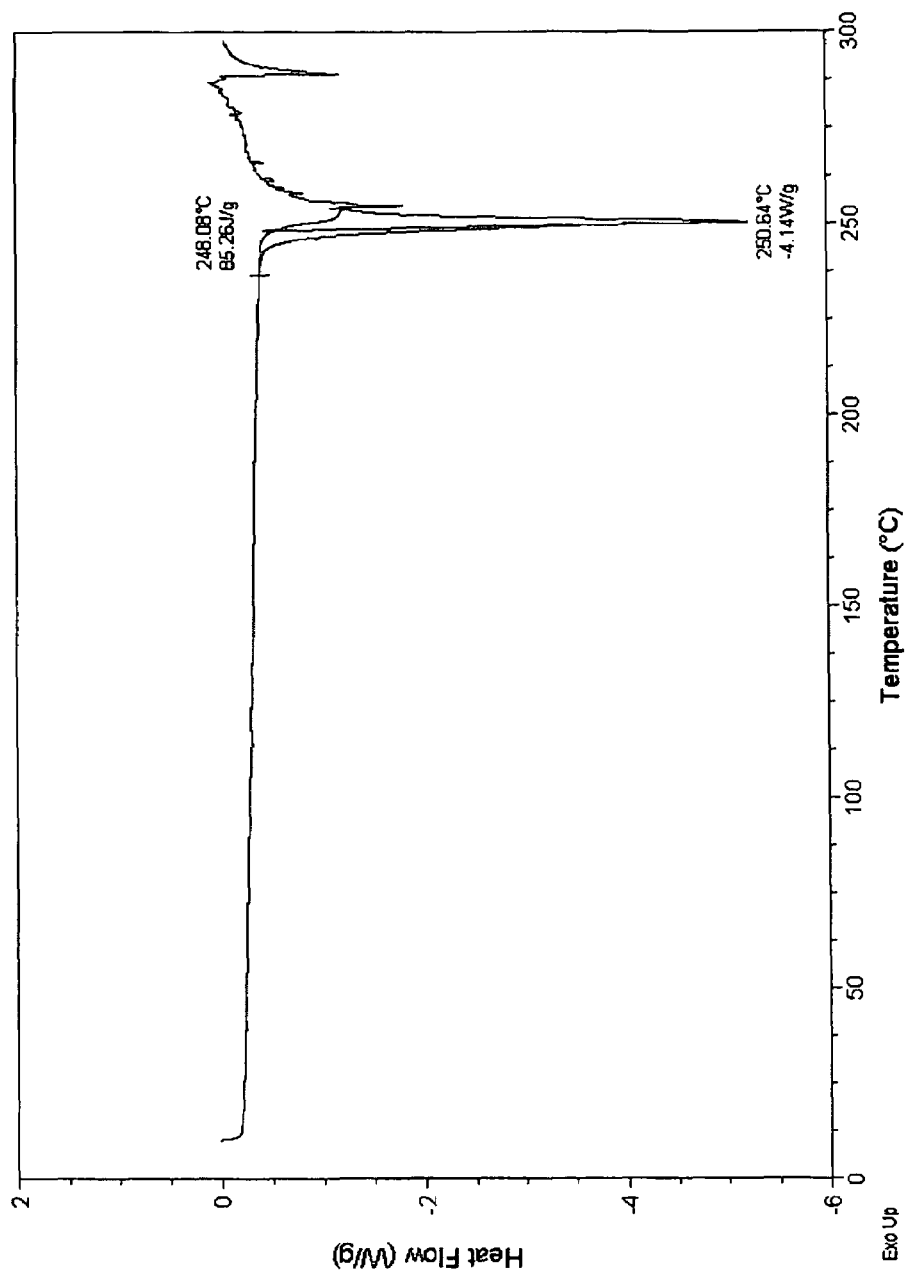

and to processes and intermediates for their preparation. The present invention also relates to pharmaceutical compositions containing these compounds, to their combination with one or more other therapeutic agents, as well as to their use for the treatment of a number of inflammatory and allergic diseases, disorders and conditions.

5 Claims, 6 Drawing Sheets

GLUCOCORTICOID RECEPTOR AGONISTS

This present invention relates to novel glucocorticoid receptor agonists and to pharmaceutically acceptable salts thereof or pharmaceutically acceptable solvates of said glucocorticoid receptor agonists or salts, processes and intermediates for their preparation. The present invention also relates to pharmaceutical compositions containing these compounds, to their combination with one or more other therapeutic agents, as well as to their use for the treatment of a number of inflammatory and allergic diseases, disorders and conditions.

Glucocorticoid receptor agonists are potent anti-inflammatory drugs that are indispensable for the treatment of a broad array of inflammatory and immunological disorders. The first compounds introduced into therapy were derived from the natural corticosteroid hydrocortisone. First structural modifications of the core molecule aimed at the increase in selectivity to the glucocorticoid over the mineralo-corticoid receptor. Based on a better understanding of structure-activity relationships, the next generation of compounds displayed higher receptor affinities and thus higher efficacy. For topically applied glucocorticoids, further progress was achieved by drug targeting e.g. by inhalation or skin application of corticosteroid preparations. Recent developments focused on the best possible reduction of adverse effects by introducing metabolically labile functional groups into the active molecule to minimize systemic exposure after topical application. High affinity to the therapeutic target tissue was recognized as a property that enhances on-target efficacy and duration of action while limiting off-target systemic effects by slowing redistribution into the systemic circulation.

Glucocorticoid receptor agonists are used in the management of inflammatory and allergic conditions, e.g. asthma, obstructive airway diseases, rhinitis, inflammatory bowel disease, psoriasis, eczema etc. Examples of already marketed glucocorticoids include:

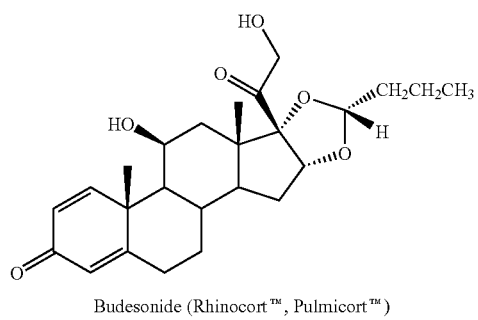

Budesonide (Rhinocort™, Pulmicort™)

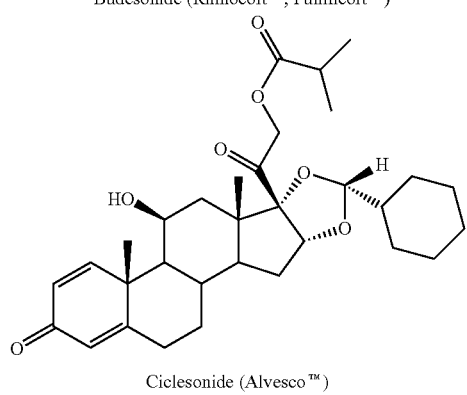

Ciclesonide (Alvesco™)

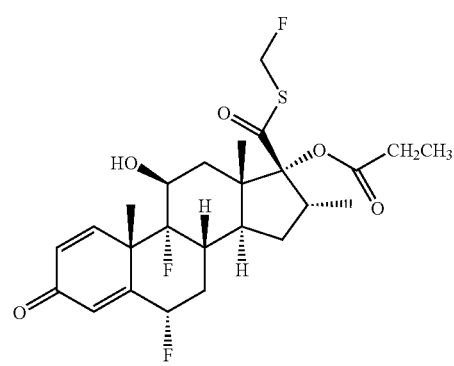

Fluticasone propionate (Flovent™, Flonase™)

These compounds bind to and activate glucocorticoid receptors in a wide range of cell types. The activated receptor binds to glucocorticoid response elements in the nucleus activating or inhibiting transcription of genes that have key regulatory functions. In particular these compounds are efficacious in inflammatory diseases by preventing the recruitment of inflammatory leukocytes, such as eosinophils and neutrophils to sites of inflammation and also inhibiting the formation and release of inflammatory mediators from leukocytes and tissue cells.

Since the marketing of the first corticosteroids, numerous corticosteroids have been proposed having different structures such as for example the compounds as described in WO05/028495 of formula:

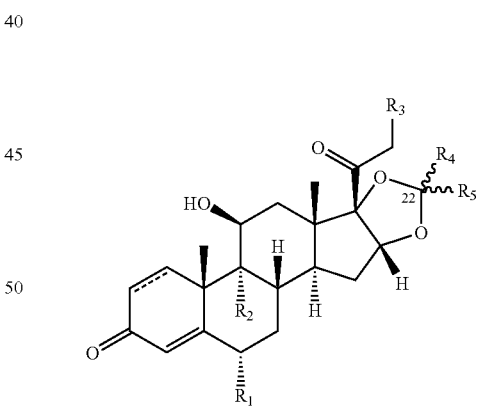

wherein --- may be a double bond, $R_1$ and $R_2$ may be F, $R_3$ may be OH, $R_4$ may be H, and $R_5$ may be a $C_{5-10}$ aryl which may be optionally substituted by a phenyl, said phenyl being optionally substituted by an alkyl, alkoxy or halogen.

However, there is still a need for improved glucocorticoid receptor agonists that would have the most appropriate pharmacological profile, for example in terms of potency, therapeutic index, pharmacokinetics, drug/drug interactions and/ or side effects. In this context, there is provided a compound of formula (I):

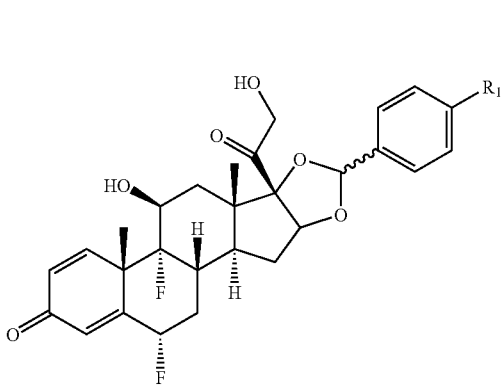

(I)

wherein R₁ is selected from the group consisting of:

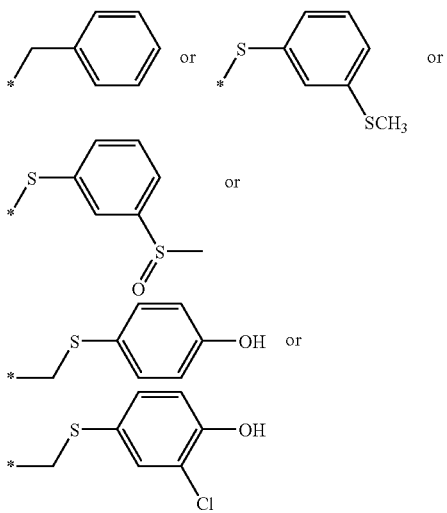

wherein * represents the attachment point of R₁ to the carbon of the phenyl cycle; or a pharmaceutically acceptable salt thereof or a pharmaceutically acceptable solvate of said compound or salt.

According to a first embodiment, the sub-group of glucocorticoid receptor agonists of formula (Ia):

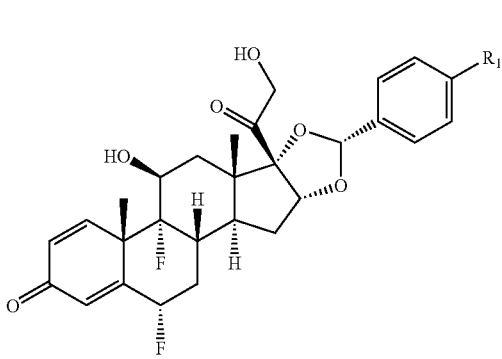

(Ia)

wherein R₁ is selected from the group consisting of:

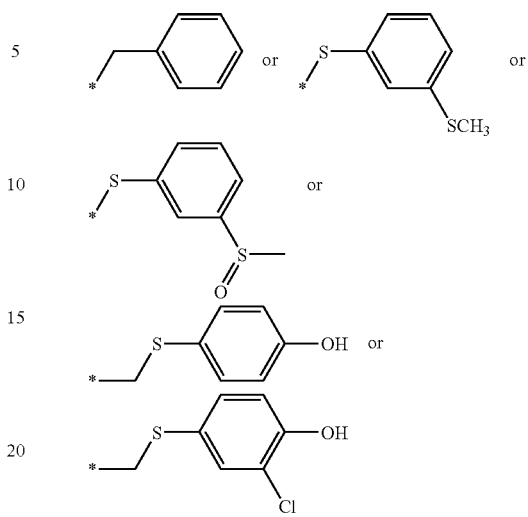

wherein * represents the attachment point of R₁ to the carbon of the phenyl cycle; or a pharmaceutically acceptable salt thereof or a pharmaceutically acceptable solvate of said compound or salt.
is preferred.

The present invention therefore covers the following preferred compounds:

(4aS,4bR,5S,6aS,6bS,8R,9aR,10aS,10bS,12S)-8-(4-benzylphenyl)-4b,12-difluoro-6b-glycoloyl-5-hydroxy-4a,6a-dimethyl-4a,4b,5,6,6a,6b,9a,10,10a,10b,11,12-dodecahydro-2H-naphtho[2',1':4,5]indeno[1,2-d][1,3]dioxol-2-one;

(4aS,4bR,5S,6aS,6bS,8R,9aR,10aS,10bS,12S)-4b,12-difluoro-6b-glycoloyl-5-hydroxy-4a,6a-dimethyl-8-(4-{[3-(methylthio)phenyl]thio}phenyl)-4a,4b,5,6,6a,6b,9a,10,10a,10b,11,12-dodecahydro-2H-naphtho[2',1':4,5]indeno[1,2-d][1,3]dioxol-2-one;

(4aS,4bR,5S,6aS,6bS,8R,9aR,10aS,10bS,12S)-4b,12-difluoro-6b-glycoloyl-5-hydroxy-8-(4-{[(4-hydroxyphenyl)thio]methyl}phenyl)-4a,6a-dimethyl-4a,4b,5,6,6a,6b,9a,10,10a,10b,11,12-dodecahydro-2H-naphtho[2',1':4,5]indeno[1,2-d][1,3]dioxol-2-one;

(4aS,4bR,5S,6aS,6bS,8R,9aR,10aS,10bS,12S)-4b,12-difluoro-6b-glycoloyl-5-hydroxy-4a,6a-dimethyl-8-(4-{[3-(methylsulfinyl)phenyl]thio}phenyl)-4a,4b,5,6,6a,6b,9a,10,10a,10b,11,12-dodecahydro-2H-naphtho-[2',1':4,5]indeno[1,2-d][1,3]dioxol-2-one; and (4aS,4bR,5S,6aS,6bS,8R,9aR,10aS,10bS,12S)-8-(4-{[(3-chloro-4-hydroxyphenyl)thio]methyl}phenyl)-4b,12-difluoro-6b-glycoloyl-5-hydroxy-4a,6a-dimethyl-4a,4b,5,6,6a,6b,9a,10,10a,10b,11,12-dodecahydro-2H-naphtho[2',1':4,5]indeno[1,2-d][1,3]dioxol-2-one.

A further preferred glucocorticoid receptor agonist according to the present invention is (4aS,4bR,5S,6aS,6bS,8R,9aR,10aS,10bS,12S)-4b,12-difluoro-6b-glycoloyl-5-hydroxy-4a,6a-dimethyl-8-(4-{[3-(methylthio)phenyl]thio}phenyl)-4a,4b,5,6,6a,6b,9a,10,10a,10b,11,12-dodecahydro-2H-naphtho[2',1':4,5]indeno[1,2-d][1,3]dioxol-2-one.

Another preferred glucocorticoid receptor agonist according to the present invention is (4aS,4bR,5S,6aS,6bS,8R,9aR,10aS,10bS,12S)-4b,12-difluoro-6b-glycoloyl-5-hydroxy-8-(4-{[(4-hydroxyphenyl)thio]methyl}phenyl)-4a,6a- dimethyl-4a,4b,5,6,6a,6b,9a,10,10a,10b,11,12-dodecahydro-2H-naphtho[2',1':4,5]indeno[1,2-d][1,3]dioxol-2-one.

Still another preferred glucocorticoid receptor agonist according to the present invention is (4aS,4bR,5S,6aS,6bS,8R,9aR,10aS,10bS,12S)-8-(4-{[(3-chloro-4-hydroxyphenyl)thio]methyl}phenyl)-4-b,12-difluoro-6b-glycoloyl-5-hydroxy-4a,6a-dimethyl-4a,4b,5,6,6a, 6b,9a,10,10a,10b,11,12-dodecahydro-2H-naphtho[2',1':4,5]indeno[1,2-d][1,3]dioxol-2-one.

The compounds of formula (I) according to the present invention may be prepared in a variety of ways using conventional procedures such as by the following illustrative methods in which $R_1$ is as previously defined for the compounds of the formula (I) unless otherwise stated. But the skilled person will appreciate that other routes may be equally as practicable.

The compounds of formula (I) may be prepared according to scheme 1 as follows:

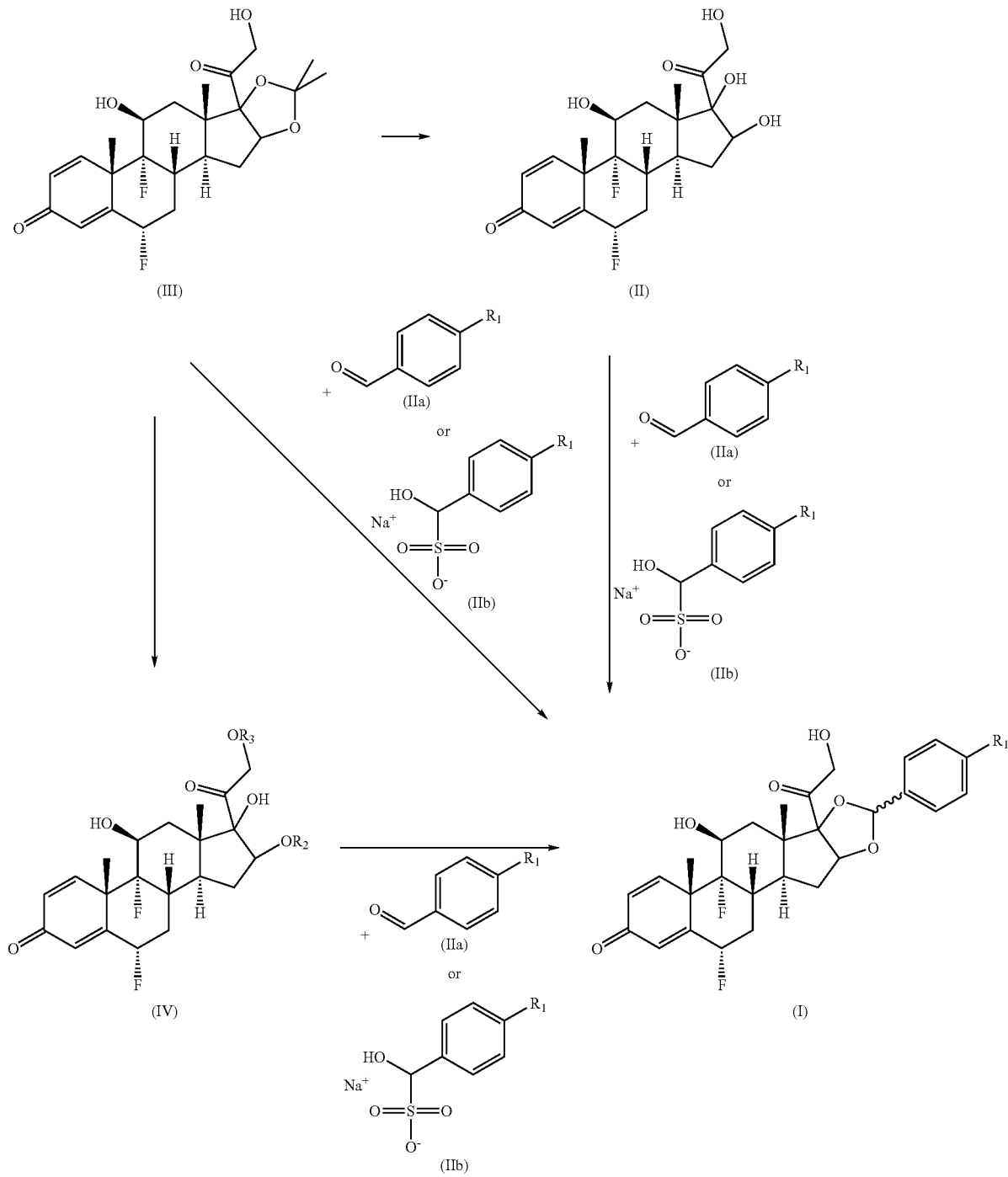

According to scheme 1, the compounds of formula (I) may be prepared by the reaction of a compound of formula (II) with a suitable aldehyde of formula (IIa) or with a suitable aldehyde equivalent of formula (IIb). Conveniently the reaction is effected by using an excess of the aldehyde or aldehyde equivalent or stoichiometric quantity of the aldehyde or aldehyde equivalent in the presence of an acid such as an alkyl sulphonic acid (e.g. trifluoromethanesulphonic acid), in the presence of a suitable solvent (e.g. acetonitrile, ethylene glycol dimethyl ether, 1,4-dioxane or dichloromethane), optionally in the presence of a drying agent (such as magnesium sulphate or sodium sulphate), and at ambient temperature or reduced temperature.

The compound of formula (II) may be prepared by the reaction of the compound of formula (III) by methods known in the literature (e.g. Fried, J. U.S. Pat. No. 3,177,231 (1965)) or by treatment with aqueous hydrofluoroboric acid and at ambient or elevated temperature, such as 40° C.

Alternatively, the compound of formula (I) wherein $R_1$ is of formula:

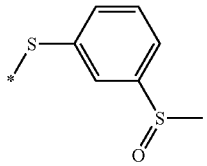 [SMILES: *Sc1cccc(S(C)=O)c1]

may also be prepared by reaction of the compound of formula (I) wherein $R^1$ is of formula:

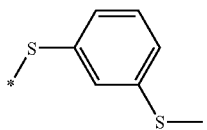

with a suitable oxidising agent. Conveniently the reaction is effected by using a slight excess of oxidising agent, such as hydrogen peroxide, in the presence of a suitable solvent (e.g. hexafluoroisopropanol), and at ambient temperature or reduced temperature (see Tet. Lett., 39, 3141-3144, by J. P. Begue et al, 1998).

Compounds of formula (I) may also be prepared by reaction of the compound of formula (III) with a suitable aldehyde of formula (IIa) or with a suitable or aldehyde equivalent of formula (IIb). Conveniently reaction is effected by using an excess of the aldehyde or aldehyde equivalent or stoichiometric quantity of the aldehyde or aldehyde equivalent in the presence of an acid (such as e.g. trifluoromethanesulphonic acid or perchloric acid); in the presence of a suitable solvent (such as e.g. acetonitrile or 1,4-dioxane); optionally in the presence of an additive (such as e.g. sand) and at ambient temperature or reduced temperature.

Compounds of formula (I) may also be prepared by reaction of the compound of formula (IV) wherein $R_2$ and $R_3$ are defined as formyl, with a suitable aldehyde of formula (IIa) or with a suitable aldehyde equivalent of formula (IIb) by methods known in the literature (e.g. WO2005/028495).

The compounds of formula (IV) wherein $R_2$ and $R_3$ are defined as formyl, may be prepared by the reaction of compounds of formula (III) by methods known in the literature (e.g. WO2005/028495).

The compound of formula (III) is commercially available.

According to the present invention, a "suitable aldehyde" means an aldehyde of formula (IIa):

wherein $R_1$ is as previously defined for the compounds of formula (I). In other words, the suitable aldehyde according to the present invention is selected from the group consisting of:

4-Benzylbenzaldehyde of formula (Va):

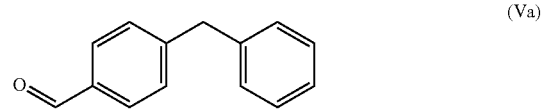 [SMILES: O=Cc1ccc(Cc2ccccc2)cc1]

4-{[3-(Methylthio)phenyl]thio}benzaldehyde of formula (VIa):

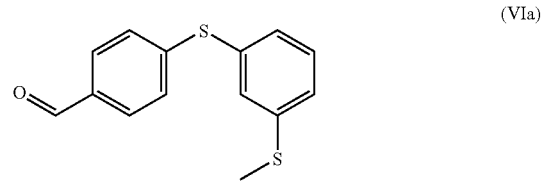 [SMILES: CSc1cccc(Sc2ccc(C=O)cc2)c1]

4-{[(4-Hydroxyphenyl)thio]methyl}benzaldehyde of formula (VIIa):

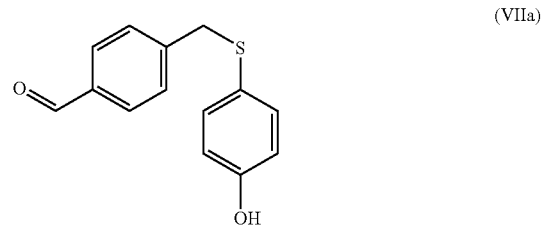 [SMILES: O=Cc1ccc(CSc2ccc(O)cc2)cc1]

4-{[3-(Methylsulphinyl)phenyl]thio}benzaldehyde of formula (VIIIa):

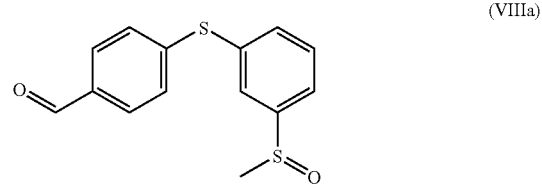 [SMILES: CS(=O)c1cccc(Sc2ccc(C=O)cc2)c1]

or 4-{[(3-chloro-4-hydroxyphenyl)thio]methyl}benzaldehyde of formula (IXa):

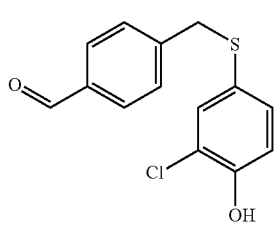

(IXa)

Alternatively, a "suitable aldehyde equivalent" means a compound of formula (IIb):

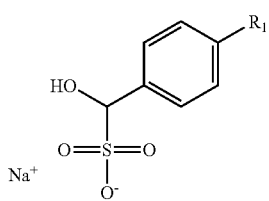

(IIb)

which may also be referred to as a "bisulfite adduct", wherein $R_1$ is as previously defined for the compounds of formula (I). In other words, the suitable aldehyde equivalent according to the present invention is selected from the group consisting of:

Sodium hydroxyl(benzylphenyl)methanesulfonate of formula (Vb):

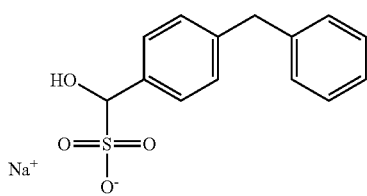

(Vb)

Sodium hydroxy(4-{[3-(methylthio)phenyl]thio}phenyl)methanesulfonate (VIb):

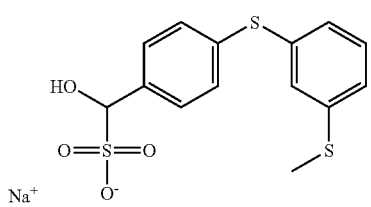

(VIb)

Sodium hydroxyl(4-{[(4-hydroxyphenyl)thio]methyl}phenyl)methanesulfonate of formula (VIIb):

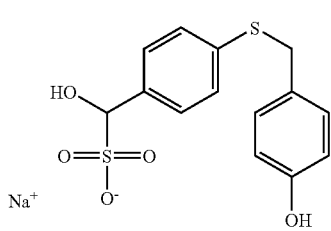

(VIIb)

Sodium hydroxy(4-{[4-(methylsulfinyl)phenyl]thio}phenyl)methanesulfonate of formula (VIIIb):

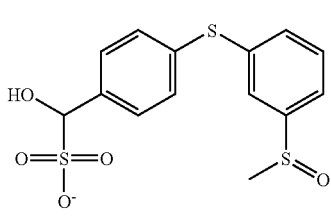

(VIIIb)

or Sodium (4-{[(3-chloro-4-hydroxyphenyl)thio]methyl}phenyl)(hydroxy)methanesulfonate of formula (IXb):

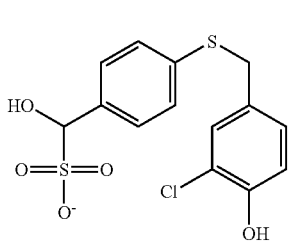

(IXb)

The above mentioned aldehydes or aldehyde equivalents are either commercially available or may be easily prepared according to conventional procedures well known to the skilled person.

For some of the steps of the here above described process of preparation of the compounds of formula (I), it may be necessary to protect potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by P. J. Kocienski (*Protecting groups*, Georg Thieme Verlag, 1994), can be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of formula (I) as well as intermediate for the preparation thereof can be purified according to various well-known methods, such as for example crystallization or chromatography.

Pharmaceutically acceptable salts of the compounds of formula (I) include the base salts thereof. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Pharmaceutically acceptable salts of the compounds of formula (I) may also eventually include the acid salts thereof. Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention and salts thereof may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, $4^{th}$ Edition (Edward Arnold, 1970).

Hereinafter all references to the compounds of the invention include references to salts, solvates, multi-component complexes and liquid crystals thereof and to solvates, multi-component complexes and liquid crystals of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'prodrugs' of the compounds of the invention are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include, where the compound of formula (I) contains an alcohol functionality (—OH), an ether thereof, for example, a compound wherein the hydrogen of the alcohol functionality of the compound of formula (I) is replaced by ($C_1$-$C_6$)alkanoyloxymethyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include:
(i) where the compound of formula (I) contains a methyl group, an hydroxymethyl derivative thereof (—$CH_3$→—$CH_2OH$);

(ii) where the compound of formula (I) contains a phenyl moiety, a phenol derivative thereof (-Ph→-PhOH); and
(iii) where the compound of formula (I) contains a sulfide, a sulfoxide derivative thereof (—SPh→—S(O)Ph).

Compounds of formula (I) containing one or more asymmetric carbon atoms can exist as two or more stereoisomers. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism. Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (I) should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention such as for example diluents, carriers and adjuvants. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line,* 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula I, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (I). The overall daily dose will typically be in the range 0.001 mg to 40 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of formula (I) according to the present invention are particularly suitable for nasal, inhaled and topical administration.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg, preferably in the range of 0.01 mg to 1000 mg, depending, of course, on the mode of administration. For example, oral administration or intravenous, intramuscular, intra-articular or peri-articular administration may require a total daily dose of from 0.01 mg to 1000 mg, preferably from 0.01 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly. For the avoidance of doubt, references herein to "treatment" include references to curative, palliative and prophylactic treatment.

The compounds of formula (I) have the ability to interact with glucocorticoid receptor and thereby have a wide range of therapeutic applications, as described further below, because of the essential role which the glucocorticoid receptor plays in the physiology of all mammals.

Thus the invention relates to the compounds of formula (I), or pharmaceutically acceptable salts thereof or pharmaceutically acceptable solvates of said compounds or salts, for use in the treatment or the prevention of diseases, disorders, and conditions in which the glucocorticoid receptor is involved. The invention further relates to the use of the compounds of formula (I), or pharmaceutically acceptable salts thereof or pharmaceutically acceptable solvates of said compounds or salts, for the manufacture of a medicament for the treatment of diseases, disorders, and conditions in which the glucocorticoid receptor is involved. The invention also further relates to a method of treatment of a mammal, including a human being, with a glucocorticoid receptor agonist including treating said mammal with an effective amount of a compound of the formula (I) or with a pharmaceutically acceptable salt thereof or a pharmaceutically acceptable solvate of said compound or salt.

Examples of such diseases, disorders, and conditions include skin diseases such as eczema, psoriasis, dermatitis, pruritis and hypersensitivity reactions; inflammatory conditions of the nose, throat and lungs such as rhinitis, sinusitis, asthma, nasal polyps, chronic obstructive pulmonary disease (COPD) and fibrosis; inflammatory diseases of the intestine such as inflammatory bowel disease, Crohn's disease and ulcerative colitis; auto-immune diseases such as rheumatoid arthritis; multiple sclerosis and disseminated lupus erythematosus; ocular conditions, such as non-infected inflammation (conjunctivitis). The compounds may also have application in cancer (e.g. gliomas and prostate cancer), acquired immunodeficiency syndrome, osteoarthritis, septic shock, graft rejection, emphysema (especially by patients having COPD), post-ischaemic lesions, pulmonary hypertension, acute respiratory distress syndrome, prevention of restenosis after coronary angioplasty, Stevens-Johnson syndrome, HELLP syndrome (a variant form of severe pre-eclampsia), pneumonia, chronic active hepatitis, haematological disorders, renal disease, and acute spinal cord injury.

More specifically, the compounds according to the present invention are useful for the treatment of skin diseases such as eczema, psoriasis, dermatitis, pruritis and hypersensitivity reactions; inflammatory conditions of the nose, throat and lungs such as rhinitis, sinusitis, asthma, nasal polyps, chronic obstructive pulmonary disease (COPD) and fibrosis; inflammatory diseases of the intestine such as inflammatory bowel disease, Crohn's disease and ulcerative colitis; and auto-immune diseases such as rheumatoid arthritis; and ocular conditions, such as conjunctivitis.

More specifically, the present invention also concerns the compounds of formula (I), or pharmaceutically acceptable salts thereof or pharmaceutically acceptable solvates of said compounds or salts, for use in the treatment of diseases, disorders, and conditions selected from the group consisting of:

skin diseases of whatever type, etiology, or pathogenesis, in particular eczema, psoriasis, allergic dermatitis, neurodermatitis. pruritis and hypersensitivity reactions;

eye conditions, such as non-infected ocular inflammation (conjunctivitis);

seasonal allergic rhinitis or perennial allergic rhinitis or sinusitis of whatever type, etiology, or pathogenesis, in particular sinusitis that is a member selected from the group consisting of purulent or nonpurulent sinusitis, acute or chronic sinusitis and ethmoid, frontal, maxillary, or sphenoid sinusitis;

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolitis;

obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension;

nasal polyps of whatever type, etiology, or pathogenesis;

fibrosis of whatever type, etiology, or pathogenesis, in particular pulmonary fibrosis associated with inflammatory airway disease;

inflammatory diseases of the intestine of whatever type, etiology, or pathogenesis, in particular ulcerative colitis and Crohn's disease;

auto-immune diseases of whatever type, etiology, or pathogenesis, in particular rheumatoid arthritis, multiple sclerosis, and disseminated lupus erythematosus, Even more specifically, the compounds according to the present invention are more specifically useful for the treatment of asthma, COPD, allergic rhinitis, nasal polyps, Crohn's disease, eczema, and psoriasis.

According to another embodiment of the present invention, the compounds of the invention, or pharmaceutically acceptable salts thereof or pharmaceutically acceptable solvates of said compounds or salts, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of the formula (I), or a pharmaceutically acceptable salt thereof or a pharmaceutically acceptable solvate of said compound or salt, or one or more glucocorticoid receptor agonists known in the art. More typically, the second and more therapeutic agents will be selected from a different class of therapeutic agents.

As used herein, the terms "co-administration", "co-administered" and "in combination with", referring to the compounds of the invention and one or more other therapeutic agents, is intended to mean, and does refer to and include the following:

simultaneous administration of such combination of compound(s) of formula (I) and therapeutic agent(s) to a patient in need of treatment, when such components are formulated together into a single dosage form which releases said components at substantially the same time to said patient, substantially simultaneous administration of such combination of compound(s) of formula (I) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (I) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (I) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compounds of the invention, or pharmaceutically acceptable salts thereof or pharmaceutically acceptable solvates of said compounds or salts, include, but are by no means limited to:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Inhibitors of leukotriene C4 synthase,
(d) Histamine receptor antagonists including H1, H3 and H4 antagonists,
(e) $\alpha_1$- and $\alpha_2$-adrenoceptor agonist vasoconstrictor sympathomimetic agents for decongestant use,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Prostaglandin receptor antagonists and inhibitors of prostaglandin synthase such as hPGDS,
(k) Muscarinic M3 receptor antagonists or anticholinergic agents,
(l) β2-adrenoceptor agonists;
(m) Monoclonal antibodies active against endogenous proinflammatory entities such as e.g. IgE, IL3, IL4, IL9, IL10, IL13, IL17A, GMCSF and their receptors,
(n) Anti-tumor necrosis factor (anti-TNF-α) agents,
(o) Adhesion molecule inhibitors including VLA-4 antagonists,
(p) Kinin-$B_1$- and $B_2$-receptor antagonists,
(q) Immunosuppressive agents, including inhibitors of the IgE pathway and cyclosporine,
(r) Inhibitors of matrix metalloproteases (MMPs) such as e.g. MMP9 and MMP12,
(s) Tachykinin $NK_1$, $NK_2$ and $NK_3$ receptor antagonists,
(t) Protease inhibitors such as elastase inhibitors, in particular neutrophil elastase inhibitors,
(u) Adenosine A2a receptor agonists and A2b antagonists,
(v) Inhibitors of urokinase,
(w) Compounds that act on dopamine receptors, such as D2 agonists,
(x) Modulators of the NFκβ pathway, such as IKK inhibitors,
(y) modulators of cytokine signalling pathways such as p38 MAP kinase, PI3 kinases, JAK kinases, syk kinase, EGFR, MK-2, fyn kinases or ITK,
(z) Agents that can be classed as mucolytics or anti-tussive,
(aa) Agents, which enhance or re-sensitise responses to inhaled corticosteroids, such as e.g. macolide analogues and inhibitors of PI3Kδ or AKT1,2,3,
(bb) Antibiotics and antiviral agents effective against micro-organisms which can colonise the respiratory tract, (cc) HDAC activators,
(dd) CXCR1, CXCR2 and CXCR3 antagonists,
(ee) Integrin antagonists,
(ff) Chemokines and chemokine receptor antagonists,
(gg) Epithelial sodium channel (ENaC) blockers or Epithelial sodium channel (ENaC) inhibitors,
(hh) CRAC ion channel blockers or CRAC inhibitors,
(ii) P2Y2 Agonists and other Nucleotide receptor agonists,
(jj) P2X7 antagonists,
(kk) Inhibitors of VAP1,
(ll) Inhibitors of thromboxane,
(mm) Niacin, and
(nn) Adhesion factors including VLAM, ICAM, and ELAM.

According to the present invention, the combination of the compounds of formula (I) with:
muscarinic M3 receptor agonists or anticholinergic agents including e.g. ipratropium salts, namely bromide, tiotropium salts, namely bromide, oxitropium salts, namely bromide, trospium salts, aclidinium salts, perenzepine, and telenzepine,
β2-adrenoceptor agonists including e.g. ephedrine, adrenaline, isoprenaline, metaproterenol, phenylephrine, phenylpropanolamine, pirbuterol, reproterol, rimiterol, isoetharine, tolobuterol, carmoterol, albuterol, terbutaline, bambuterol, fenoterol, salbutamol, tulobuterol formoterol, salmeterol, and the agonists described in WO 05/080313, WO 05/080324, WO 05/092840 and WO2007/010356;
PDE4 inhibitors, in particular inhaled PDE4 inhibitors,
Theophylline,
Histaminic receptor antagonists including H1 and H3 antagonists, e.g. loratadine and methapyrilene; or
adenosine A2a receptor agonists, e.g. those described in WO01/94368 is preferred.

According to a preferred aspect, the compounds of the present invention may be combined with another therapeutic agent selected from β2-adrenoceptor agonists and anticholinergic agents. Another preferred aspect includes the triple combination of a compound according to the present invention together with a P2-adrenoceptor agonist and an anticholinergic agent.

The following non-limiting examples illustrate the invention:

FIGURES

FIG. 1/6: DSC thermogram of Example 1
FIG. 2/6: PXRD Pattern of Example 1
FIG. 3/6: DSC Thermogram for Example 2
FIG. 4/6: PXRD Pattern of Example 2
FIG. 5/6: DSC thermogram of Example 5
FIG. 6/6: PXRD pattern of Example 5

PROTOCOLS

For all examples below, the following experimental conditions were used:
Differential Scanning Calorimetry (DSC)
Differential Scanning Calorimetry was performed using a TA Instrument Q1000 DSC in aluminium pans with lids. Approximately 3 mg of the samples were heated at 20° C. per minute over ranges of 10° C. to 250° C. or 10° C. to 300° C. or 20° C. to 300° C. depending on the samples, with a nitrogen gas purge.
Powder X-Ray Diffraction Method (PXRD)
The powder X-ray diffraction pattern was determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background cavity silicon wafer specimen mount. The specimen was rotated whilst being irradiated with copper K-alpha$_1$ X-rays (wavelength=1.5406 Angstroms) with the X-ray tube operated at 40 kV/35 mA. The analyses were performed with the goniometer running in continuous mode set for a 0.2 second count per 0.018° step over a two theta range of 2° to 55°.

EXAMPLES

Preparation 1

(6α,11β,16α)-6,9-Difluoro-11,16,17,21-tetrahydroxypregna-1,4-diene-3,20-dione

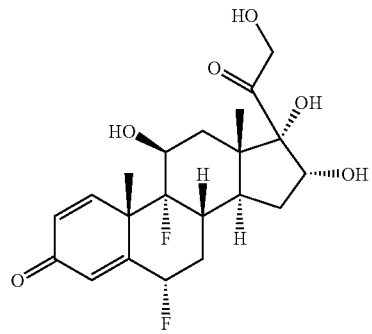

(4bR,6bS,9aR,12S)-4b,12-Difluoro-6b-glycoloyl-5-hydroxy-4a,6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one (10.3 g, 22.76 mmol—commercially available) was suspended in 48% aqueous hydrofluoroboric acid (100 mL) and the resulting suspension stirred at ambient temperature under an atmosphere of nitrogen for 7 hours. The suspension was then diluted with water (200 mL), filtered and the solid washed with water (500 mL). The solid cake was suspended in methanol (200 mL) and concentrated in vacuo. The resulting solid was suspended in tert-butyl-methyl ether (150 mL), filtered and washed with tert-butyl methyl ether (200 mL) to yield the title compound as a white solid, 95% yield, 8.9 g.

$^1$H NMR (400 MHz, DMSO-d$_6$) δ: 0.82 (s, 3H), 1.46 (s, 3H), 1.31-1.51 (m, 3H), 1.77-1.87 (m, 1H), 2.08-2.33 (m, 3H), 2.37-2.46 (m, 1H), 4.08 (d, 1H), 4.09-4.16 (m, 1H), 4.48 (d, 1H), 4.63 (br, 1H), 4.75 (dd, 1H), 5.35 (d, 1H), 5.51-5.69 (m, 1H), 6.08 (s, 1H), 6.26 (d, 1H), 7.24 (dd, 1H) ppm.
LRMS (ESI): m/z 411 [M–H]$^-$ Preparation 2

4-Benzylbenzaldehyde

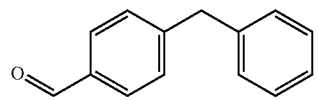 [SMILES: O=Cc1ccc(Cc2ccccc2)cc1]

Benzyl bromide (41 g, 240 mmol), 4-formylbenzeneboronic acid (28 g, 186.7 mmol), palladium tetrakis triphenyl phosphine (7.9 g, 6.84 mmol) and potassium carbonate (84.7 g, 613 mmol) were combined in tetrahydrofuran (620 mL) and heated at 80° C. under nitrogen for 8 hours. The resulting suspension was allowed to cool to ambient temperature and stirred overnight. The reaction mixture was poured into 10% citric acid (50 mL) and extracted with ethyl acetate (3-fold 50 mL). The combined organic extracts were washed with brine (100 mL) and dried (magnesium sulphate) and the solvent removed in vacuo. The resulting oil was purified by column chromatography on silica gel eluting with ethyl acetate:heptane, (0:1 changing to 1:5, by volume) to give the title compound as a colourless oil, 83% yield, 30.45 g.

$^1$H NMR (400 MHz, CDCl$_3$) δ: 4.06 (s, 2H), 7.38-7.17 (m, 7H), 7.83-7.79 (m, 2H), 9.97 (s, 1H) ppm.

LRMS (ESI): m/z 197 [M+H]$^+$

Preparation 3

4-{[3-(Methylthio)phenyl]thio}benzaldehyde

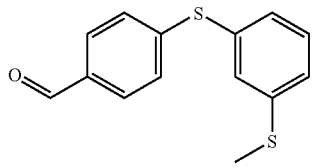 [SMILES: CSc1cccc(Sc2ccc(C=O)cc2)c1]

A solution of 3-(methylthio)benzenethiol (19.9 g, 127.3 mmol), prepared as indicated in Rumpf, P., Bull. soc. chim. (1940), 7, pp. 632-4, in acetonitrile (60 mL) was treated with 4-fluorobenzaldehyde (13.4 mL, 127 mmol) followed by potassium carbonate (19.4 g, 140 mmol). After stirring at ambient temperature for 18 hours the suspension was diluted with water (200 mL) and extracted with ethyl acetate (3-fold 300 mL). The combined organic extracts were washed with brine (2-fold 100 mL) and dried (magnesium sulphate) and the solvent removed in vacuo to give a colourless oil. The crude oil was purified by flash column chromatography on silica gel eluting with heptane:ethyl acetate (1:0 changing to 9:1, by volume) to give the title compound as a colourless oil, 33% yield, 10.8 g.

$^1$H NMR (400 MHz, CDCl$_3$) δ: 2.48 (s, 3H), 7.25-7.34 (m, 5H), 7.38 (m, 1H), 7.73-7.75 (d, 2H) ppm.

LRMS (API): m/z 261 [M+H]$^+$

Preparation 4

4-{[(4-Hydroxyphenyl)thio]methyl}benzaldehyde

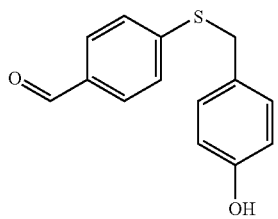 [SMILES: O=Cc1ccc(SCc2ccc(O)cc2)cc1]

A solution of 4-bromomethylbenzaldehyde (0.3 g, 1.5 mmol) and 4-hydroxythiophenol (0.2 g, 1.5 mmol) in 1,4-dioxane (10 mL) was degassed and treated with triethylamine (0.44 mL, 3.11 mmol). After stirring for 1 day the mixture was diluted with water (20 mL) and extracted with ethyl acetate (2-fold 20 mL). The combined organic extracts were washed with brine and dried (sodium sulphate) and the solvent removed in vacuo. The crude material was purified by flash column chromatography on silica gel eluting with heptane: ethyl acetate (9:1 changing to 0:1, by volume) to give the title compound as a solid, 62% yield, 220 mg.

$^1$H NMR (400 MHz, DMSO-d$_6$) δ: 4.01 (s, 2H), 6.66 (d, 2H), 7.13 (d, 2H), 7.38 (d, 2H), 7.77 (d, 2H), 9.54 (s, 1H), 9.93 (s, 1H) ppm.

LRMS (ESI): m/z 243 [M−H]$^-$

Preparation 5

3-chloro-4-hydroxyphenyl thiocyanate

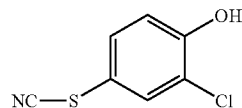

Trimethylsilyl isothiocyanate (24.5 g, 187 mmol) in hexafluoroisopropanol (10 mL) was added dropwise to an ice cold solution of 2-chlorophenol in hexafluoroisopropanol (30 mL). The reaction mixture was stirred for 10 minutes and then [Bis(trifluoroacetoxy)iodo]benzene (60.2 g, 140 mmol) was added dropwise maintaining the internal temperature below 5° C. After completion of the addition the reaction mixture was stirred for 4 hours at 5-10° C., and then concentrated in vacuo affording a yellow solid. This was taken up in dichloromethane (100 mL) and filtered through a pad of celite. The filtrate was concentrated in vacuo affording a yellow oil which was purified by flash column chromatography on silica gel eluting with dichloromethane:heptane (3:7 changing to 0:1 by volume) giving the product as a yellow solid, 30% yield, 5.2 g.

$^1$H NMR (400 MHz, CDCl$_3$) δ: 5.99 (bs, 1H), 7.06-7.10 (m, 1H), 7.40-7.43 (m, 1H), 7.59 (s, 1H).

LRMS (ESI): m/z 186 [M+H]$^+$

Alternatively, 3-chloro-4-hydroxyphenyl thiocyanate was prepared as follows:

A solution of bromine (0.40 mL, 7.78 mmol) in acetic acid (0.80 mL) was added dropwise to a suspension of 2-chlorophenol (1.00 g, 7.78 mmol) and sodium thiocyanate (2.27 g, 28.0 mmol) in acetic acid (6 mL). The internal temperature was kept between 16° C. and 25° C. during the addition. The reaction mixture was stirred at ambient temperature for 1 hour. 30 mL of water and 30 mL of ethyl acetate were then added to the reaction mixture and it was filtered through a pad of Celite®. The layers were separated and the aqueous layer extracted with ethyl acetate (2-fold 30 mL). The combined organic layers were dried (magnesium sulphate) and concentrated in vacuo affording an orange semisolid. This was taken up in 50 mL ethyl acetate and filtered through a second pad of Celite® affording 1.31 g dark orange oil. This material was used in preparation 6 without further purification.

Preparation 6

2-chloro-4-mercaptophenol

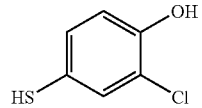

Lithium aluminium hydride (as a 1M solution in tetrahydrofuran, 71.0 ml, 71.0 mmol) was added dropwise to an ice cold solution of 3-chloro-4-hydroxyphenyl thiocyanate (4.20 g, 22.6 mmol) in tetrahydrofuran (100 mL) under nitrogen. The reaction mixture was stirred and allowed to warm to room temperature over 5 hours. The mixture was cooled to 5° C. and quenched with a 1:1 mixture of tetrahydrofuran:water until no more gas evolution was seen. 1N hydrochloric acid solution in water (30 mL) was then added, and the mixture extracted with ethyl acetate (2-fold 70 mL). The combined organic layers were dried (sodium sulphate) and concentrated in vacuo affording a colourless crystalline solid, 100% yield, 3.60 g.

$^1$H NMR (400 MHz, CDCl$_3$) δ: 3.42 (s, 1H), 5.67, (bs, 1H), 6.89-6.92 (m, 1H), 7.13-7.16 (m, 1H), 7.33 (s, 1H).

LRMS (ESI): m/z 161 [M+H]$^+$

Preparation 7

4-{[(3-chloro-4-hydroxyphenyl)thio]methyl}benzaldehyde

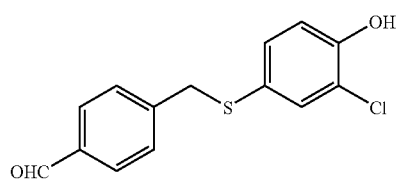 [SMILES: O=Cc1ccc(CSc2ccc(O)c(Cl)c2)cc1]

Triethylamine (5.0 mL, 35.9 mmol) was added dropwise to a solution of 2-chloro-4-mercaptophenol (3.60 g, 22.4 mmol) and 4-bromomethyl benzaldehyde (3.93 g, 19.7 mmol) in dioxane (150 mL) at room temperature under nitrogen. The reaction mixture was stirred at room temperature for 20 hours. Water (100 mL) was added to the reaction mixture and it was then partitioned with ethyl acetate and brine (200 mL each). The aqueous layer was re-extracted with ethyl acetate (100 mL). The combined organic layers were dried over sodium sulphate and concentrated in vacuo affording a yellow solid. This was purified by trituration with acetonitrile (5 mL/g) for 30 minutes. After filtration this afforded a light yellow solid as the pure product, 84% yield, 5.27 g.

$^1$H NMR (400 MHz, CDCl$_3$) δ: 3.96 (s, 2H), 5.55 (bs, 1H), 6.82-6.86 (m, 1H), 7.02-7.06 (m, 1H), 7.19-7.23 (m, 1H), 7.24-7.28 (m, 1H), 7.71-7.74 (m, 2H), 9.92 (s, 1H).

LRMS (ESI): m/z 279 [M+H]$^+$

Preparation 8

3-(Methylthio)benzenethiol

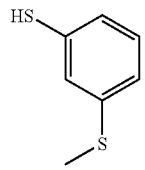

A solution of benzene-1,3-dithiol (50 g, 0.351 mmol) in 2-methyltetrahydrofuran (375 mL, 0.351 mmol) was treated with dimethylsulfate (33.3 mL, 0.351 mol) followed by 2-methyltetrahydrofuran (25 mL, used as line wash). The resulting solution was cooled to between 0° C. and 5° C. and sodium hydroxide (2M aqueous solution, 210.6 mL) was added drop wise maintaining the temperature of the reaction mixture below 15° C. followed by 2-methyltetrahydrofuran (25 mL, used as line wash) and heated under nitrogen to 50° C. for 4 hours. After cooling to ambient temperature the resulting solution was treated with tert-butylmethylether (500 mL) and the phases were separated. The organic phase was extracted with sodium hydroxide (2 M aqueous solution, 250 mL) and the combined aqueous phases were cooled to 10° C. and hydrochloric acid (6M aqueous solution, 500 mL) was added whilst maintaining the temperature of the mixture below 25° C. The resulting solution was extracted with tert-butylmethylether (2-fold 250 mL) and the combined organic phases were washed with water (500 mL) and concentrated in vacuo to give the title compound as a yellow oil, 78% yield, 42.9 g.

This material was found to be identical by HPLC to material prepared by the method of Rumpf (Bull. soc. chim. (1940), 7, pp. 632-4).

Preparation 9

Sodium hydroxy(4-{[3-(methylthio)phenyl]thio}phenyl)methanesulfonate

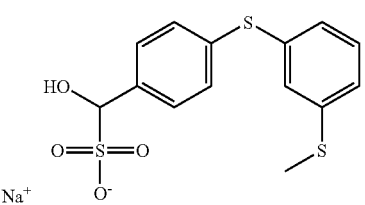 [SMILES: CSc1cccc(Sc2ccc(C(O)S(=O)(=O)[O-])cc2)c1 ; [Na+]]

A solution of 3-(methylthio)benzenethiol as prepared in Preparation 8 (290 g, 1.856 mol) in acetonitrile (3 L) was sparged with nitrogen for 1 hour and then treated with 4-fluorobenzaldehyde (196 mL, 1.856 mol) followed by acetonitrile (150 mL, used as a line wash). The resulting solution was treated with 1,1',3,3'-tetramethylguanidine (256 mL, 2.04 mol) followed by acetonitrile (150 mL used as a line wash) and heated to 50° C. under nitrogen for 16 hours. The resulting solution was allowed to cool to ambient temperature and diluted with ethyl acetate (3 L) and washed with hydrochloric acid (2M aqueous solution, 1.5 L) and sodium bicarbonate (1 M aqueous solution, 3 L) and brine (half saturated, 1.5 L). The resulting solution was concentrated by distillation at atmospheric pressure to a volume of 2 L and diluted with acetonitrile (3 L). the resulting solution was concentrated by distillation at atmospheric pressure to a volume of 2 L and diluted with acetonitrile (3 L) and concentrated by distillation at atmospheric pressure to a final volume of 3 L. The resulting solution was cooled to ambient temperature and treated with a solution of sodium metabisulfite (377 g, 1.982 mol) in water (3 L). After stirring at ambient temperature for 48 hours the resulting suspension was filtered and the solid collected was washed with water (2-fold 2.5 L) and acetonitrile (2-fold 2.5 L). The solid was suspended in acetonitrile (2 L) and stirred at ambient temperature for 18 hours after which time the suspension was filtered and the solid was washed with acetonitrile (2-fold 1 L) and dried in vacuo at 50° C. to give the title compound as a white solid, 55% yield, 368.7 g.

$^1$H NMR (400 MHz, DMSO-d$_6$) δ: 2.41 (s, 3H), 4.97 (d, 1H), 5.90 (d, 1H), 6.98 (m, H), 7.12 (m, 2H), 7.26 (m, 3H), 7.46 (d, 2H) ppm.

Example 1

(4aS,4bR,5S,6aS,6bS,8R,9aR,10aS,10bS,12S)-8-(4-Benzylphenyl)-4b,12-difluoro-6b-glycoloyl-5-hydroxy-4a,6a-dimethyl-4a,4b,5,6,6a,6b,9a,10,10a,10b,11,12-dodecahydro-2H-naphtho[2',1':4,5]indeno[1,2-d][1,3]dioxol-2-one

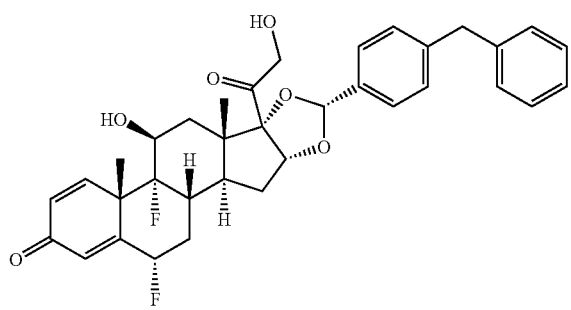

(4bR,6bS,9aR,12S)-4b,12-Difluoro-6b-glycoloyl-5-hydroxy-4a,6a,8,8-tetramethyl-4a,4b,5,6,6a,6b,9a,10,10a,10b,11,12-dodecahydro-2H-naphtho-[2',1':4,5]indeno[1,2-d][1,3]dioxol-2-one (8 g, 18 mmol) and 4-Benzylbenzaldehyde as obtained in Preparation 2 (10.4 g, 53 mmol) was added to an ice cold stirred suspension of sand (80 g) in toluene (80 mL). 70% aqueous perchloric acid (4 mL, 70 mmol) was added drop wise over 5 minutes and then the solution stirred at ambient temperature for 21 hours. Saturated sodium bicarbonate solution (100 mL) was added to the reaction mixture, followed by ethyl acetate (100 mL) and the solution stirred and then filtered. The sand was washed with saturated sodium bicarbonate solution (50 mL), and then ethyl acetate (100 mL). The aqueous layer was separated and extracted with ethyl acetate (2-fold 50 mL), and the combined organic extracts were washed with brine (100 mL) and dried (magnesium sulphate) and the solvent removed in vacuo. The resulting viscous yellow oil (10 g) was diluted with DCM:ethyl acetate (9:1, by volume), which resulted in precipitation of solid material which was collected by filtration. After drying, the material was recrystallised from ethyl acetate:heptane (4:1, by volume) to afford white crystalline material, 44% yield, 4.36 g.

$^1$H NMR (400 MHz, DMSO-$d_6$) δ: 0.82 (s, 3H), 1.45 (s, 3H), 1.43-1.50 (m, 1H), 1.62-1.71 (m, 3H), 1.97-2.03 (m, 1H), 2.16-2.30 (m, 2H), 2.51-2.65 (m, 1H), 3.87 (s, 2H), 4.12-4.18 (m, 1H), 4.15 (dd, 1H), 4.46 (dd, 1H), 4.91 (d, 1H), 5.02 (t, 1H), 5.40 (s, 1H), 5.45 (d, 1H), 5.51-5.69 (m, 1H), 6.09 (s, 1H), 6.25 (dd, 1H), 7.10-7.24 (m, 8H), 7.29-7.32 (m, 2H) ppm.

LRMS (ESI): m/z 591 [M+H]$^+$

A sample of 1.960 mg was analysed by differential scanning calorimetry (DSC) with a ramp from 10° C. to 300° C. at 20° C./min. The DSC thermogram obtained is shown in FIG. 1 with a flat baseline and a sharp endotherm corresponding to the melt at 250.6° C.

Figure 2:
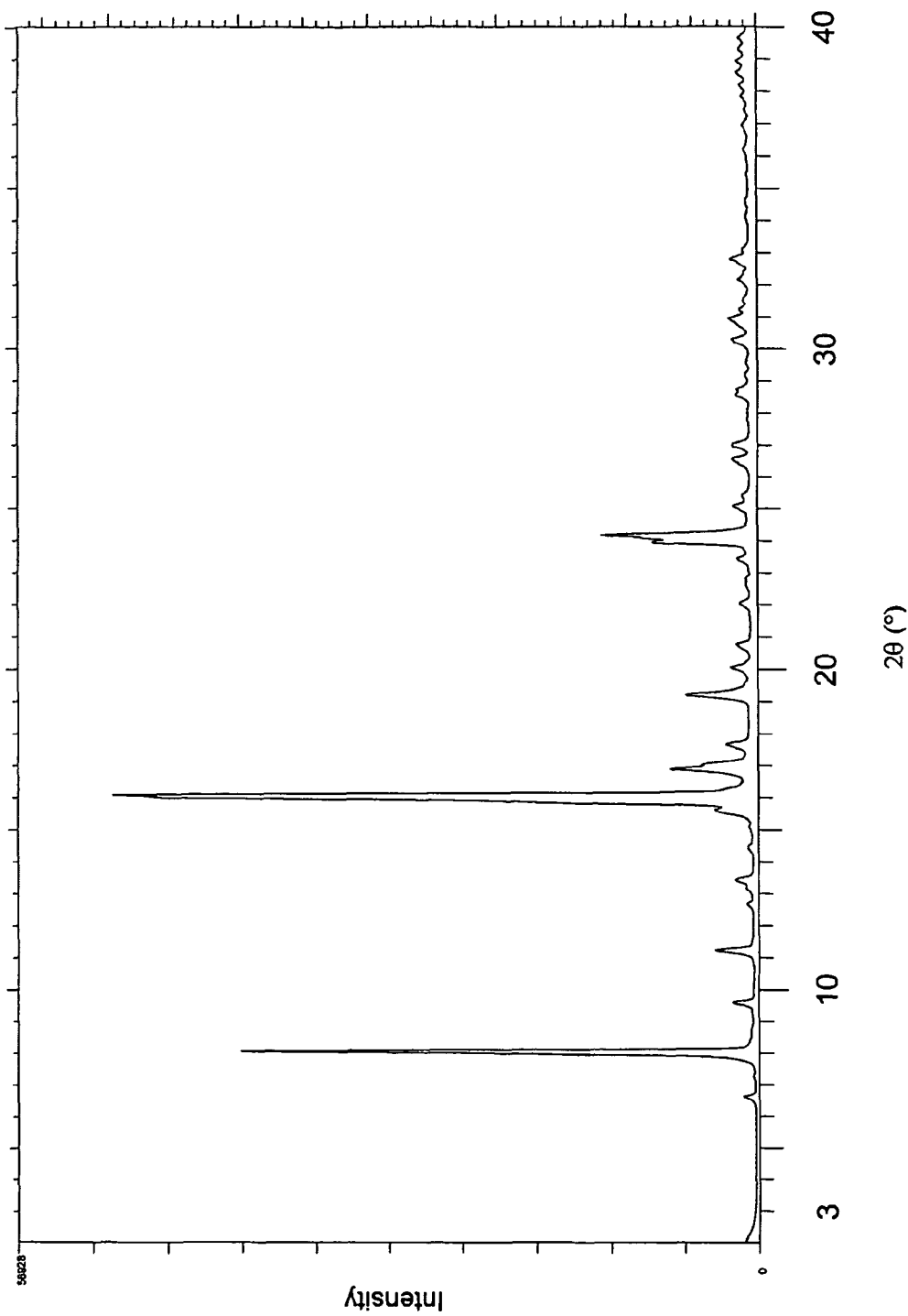

The crystalline form produced by the process described above also has the characteristics shown in the corresponding Powder X-ray diffraction pattern of FIG. 2. The main characteristic peaks are at 8.0, 16.0, 16.9, 24.0 and 24.2 degrees 2-theta±0.1 degrees 2-theta and are further given in table 1.

TABLE 1

Characteristic PXRD peaks for Example 1

| Angle 2-Theta (°±0.1) | Intensity (%) |
|---|---|
| 6.6 | 2.4 |
| 8.0 | 83.6 |
| 9.6 | 4.0 |
| 11.2 | 6.9 |
| 12.7 | 1.6 |
| 13.4 | 3.6 |
| 14.4 | 1.4 |
| 15.6 | 6.8 |
| 16.0 | 100.0 |
| 16.9 | 13.8 |
| 17.1 | 8.2 |
| 17.7 | 5.0 |
| 19.2 | 11.4 |
| 20.1 | 4.2 |
| 20.8 | 3.3 |
| 22.1 | 2.7 |
| 23.5 | 3.2 |
| 24.0 | 16.7 |
| 24.2 | 25.1 |
| 25.1 | 3.7 |
| 25.5 | 2.4 |
| 26.6 | 3.9 |
| 27.0 | 3.9 |
| 28.6 | 3.2 |
| 30.3 | 3.7 |
| 30.8 | 3.4 |
| 31.0 | 4.5 |
| 32.2 | 3.0 |
| 32.9 | 4.1 |
| 36.3 | 2.0 |
| 37.0 | 2.3 |

Example 2

(4aS,4bR,5S,6aS,6bS,8R,9aR,10aS,10bS,12S)-4b,12-difluoro-6b-glycoloyl-5-hydroxy-4a 0.6a-dimethyl-8-(4-{[3-(methylthio)phenyl]thio}phenyl)-4a,4b,5,6,6a,6b,9a,10,10a,10b,11.,12-dodecahydro-2H-naphtho[2',1':4,5]indeno[1,2-d][1,3]dioxol-2-one

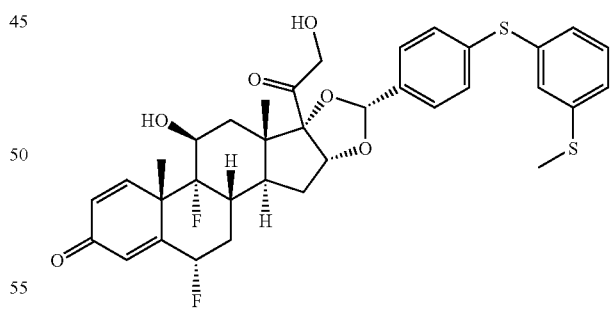

A suspension of (6α, 11β,16α)-6,9-difluoro-11,16,17,21-tetrahydroxypregna-1,4-diene-3,20-dione as obtained in Preparation 1 (6.6 g, 16 mmol) and 4-{[3-(methylthio)phenyl]thio}benzaldehyde as obtained in Preparation 3 (4.5 g, 17.28 mmol) in 1,4-dioxane (70 mL) was treated with magnesium sulphate (10 g, 83.1 mmol). The suspension was cooled in a water bath and trifluoromethanesulphonic acid (7.5 mL, 82 mmol) was added. After stirring at room temperature for 24 hours the mixture was diluted with water (200 mL) and extracted with ethyl acetate (2-fold 200 mL). The combined organic extracts were washed with water (200 mL) and brine (2-fold 150 mL) and dried (magnesium sulphate) and the solvent removed in vacuo. The crude gum was purified by flash column chromatography on silica gel eluting with heptane:tert-butyl methyl ether (4:1 changing to 1:0, by volume) then with heptane:ethyl acetate (3:7 changing to 0:1, by volume) to give a yellow foam. Further flash column chromatography on silica gel eluting with pentane:ethyl acetate (4:1 changing to 2:3, by volume) gave a yellow solid. This solid was recrystallised from 2-butanone and then from acetonitrile to give the title compound as a white solid, 18% yield, 1.93 g.

$^1$H NMR (400 MHz, DMSO-d$_6$) δ: 0.85 (s, 3H), 1.43-1.53 (m, 1H), 1.48 (s, 3H), 1.65-1.71 (m, 3H), 1.97-2.06 (m, 1H), 2.14-2.31 (m, 2H), 2.41 (s, 3H), 2.55-2.67 (m, 1H), 4.16-4.22 (m, 2H), 4.49-4.55 (dd, 1H), 4.95 (d, 1H), 5.09 (t, 1H), 5.48 (s, 1H), 5.50-5.51 (m, 1H), 5.54-5.79 (m, 1H), 6.10 (s, 1H), 6.26-6.29 (m, 1H), 7.05-7.07 (m, 1H), 7.18-7.20 (m, 2H), 7.23-7.26 (m, 1H), 7.27-7.29 (m, 1H), 7.31-7.33 (d, 2H), 7.41-7.43 (d, 2H) ppm.

LRMS (ESI): m/z 655 [M+H]$^+$

Alternatively, the title compound was prepared as follows:

A suspension of (6α, 11β,16α)-6,9-difluoro-11,16,17,21-tetrahydroxypregna-1,4-diene-3,20-dione as obtained in Preparation 1 (434 g, 1.050 mol) and magnesium sulphate (417 g, 3.47 mol) in acetonitrile (4.34 L) was stirred under nitrogen for 18 hours. Sodium hydroxy(4-{[3-(methylthio)phenyl]thio}phenyl)methanesulfonate as obtained in preparation 9 (460 g, 1.26 mol) was added and the resulting suspension was treated with trifluoromethanesulphonic acid (443 mL, 5.01 mmol) whilst maintaining the temperature of the mixture below 24° C. After stirring at ambient temperature for 75 minutes the mixture was treated with n-butyl acetate (4.4 L) and water (4.4 L) and transferred to a separator, using further n-butyl acetate (400 mL) as a line wash. The phases were separated and the organic phase was washed with water (4.4 L) and washed with sodium hydrogen carbonate (10% aqueous solution, 2-fold 2.2 L) and washed with water (2.2 L). The resulting suspension was filtered and the filtrate was concentrated in vacuo to remove 4.26 L of solvent. The residue was allowed to cool to 35° C. and treated with 2-butanone (4 L) and allowed to cool to ambient temperate and stirred for 18 hours. The resulting suspension was filtered and the solid was washed with 2-butanone (2-fold 2 L). The solid was suspended in ethanol (denatured with 2-butanone, 8 L) and heated to reflux for 10 minutes and allowed to cool to ambient temperature. The resulting suspension was filtered and the solid was washed with ethanol (denatured with 2-butanone, 2-fold 2 L) and acetonitrile (900 mL). The solid was suspended in acetonitrile (2.6 L) and heated to reflux and treated with acetonitrile (1.3 L) and concentrated by distillation at atmospheric pressure remove 2.7 L of solvent. The resulting suspension was treated with acetonitrile (1.75 L) and heated to reflux and was allowed to cool to ambient temperature. The resulting suspension was filtered and the solid was washed with acetonitrile (2-fold 450 mL) and dried in vacuo at 40° C. to give the title compound as a white solid, 37% yield, 307.3 g.

The compound thus obtained was identical as the compound obtained by previous method.

Figure 3:
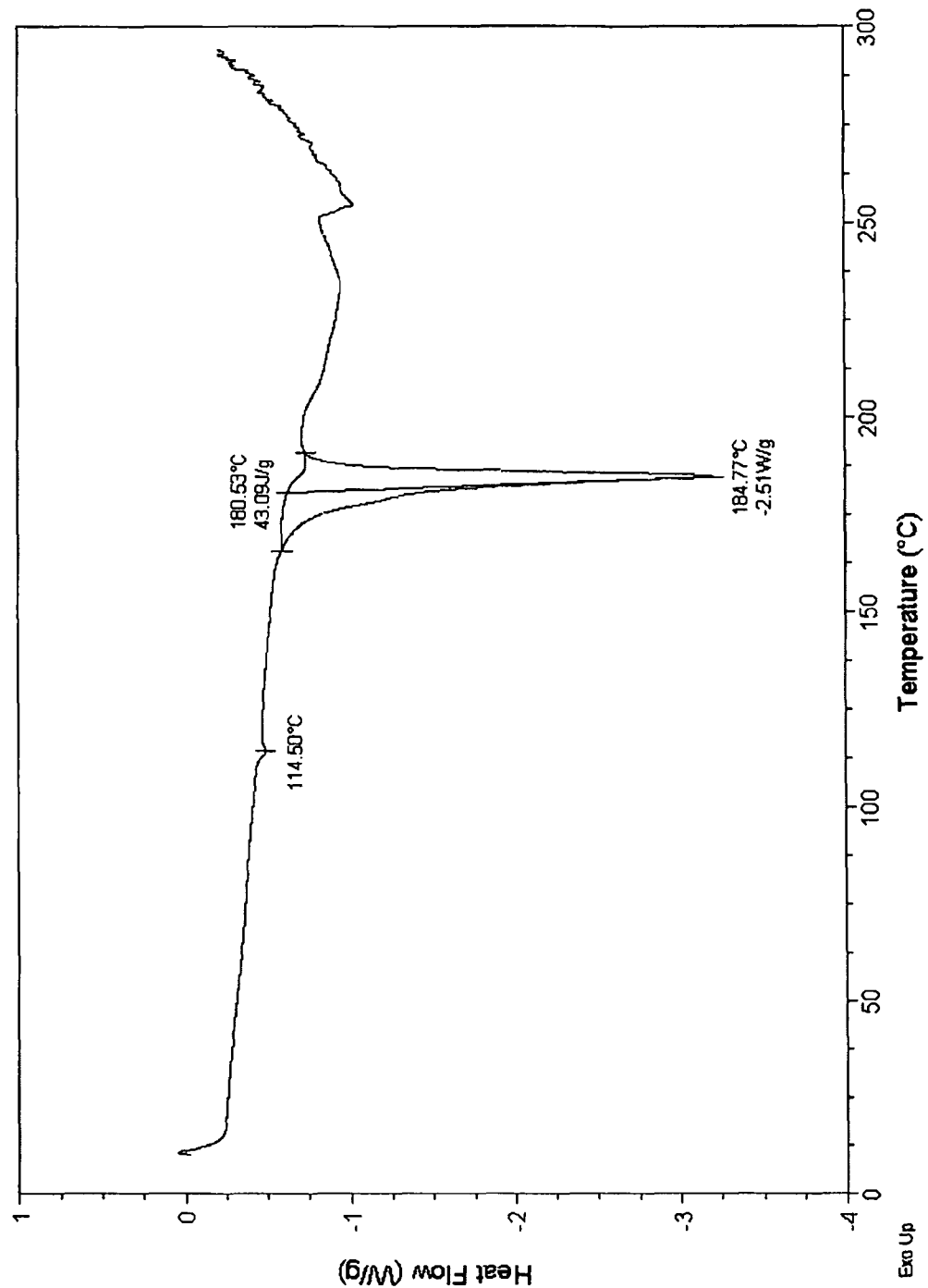

A sample of 2.847 mg of product obtained according to the 1$^{st}$ method as here above described was analysed by differential scanning calorimetry (DSC) with a ramp from 10 to 300° C. at 20° C./min. A first endothermic event has been observed at 114.5° C. which is likely to correspond to an impurity. The melt is observed at 184.8° C. The corresponding thermogram is shown in FIG. 3.

Figure 4:
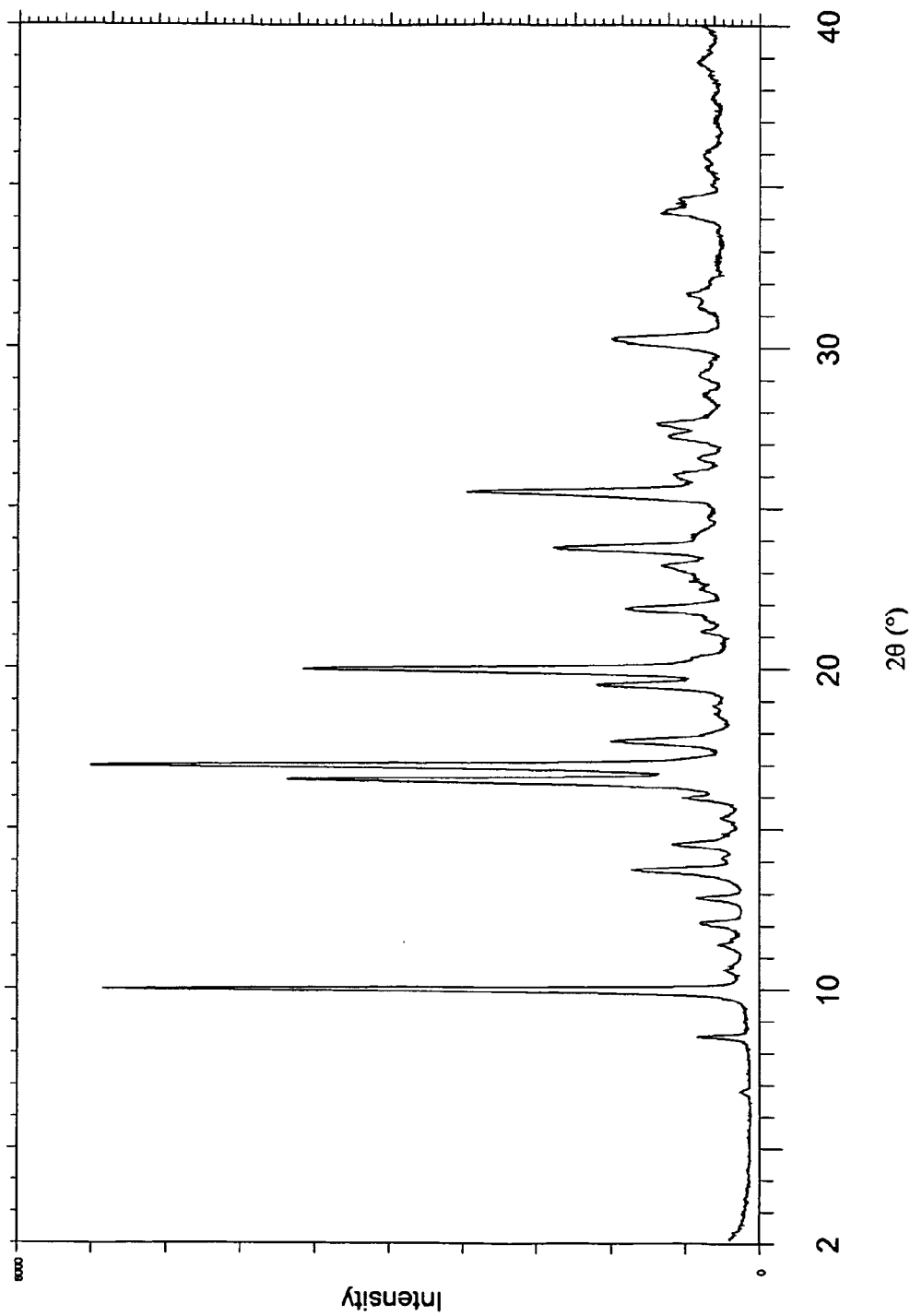

The crystalline form produced by the process described above also has the characteristics shown in the corresponding Powder X-ray diffraction pattern of FIG. 4. The main characteristic peaks are at 10.0, 16.5, 17.0, 20.0 and 25.5 degrees 2-theta±0.1 degrees 2-theta and are further given in table 2 below.

TABLE 2

Characteristic PXRD peaks for Example 2

| Angle 2-Theta (°±0.1) | Intensity (%) |
|---|---|
| 8.5 | 9.1 |
| 10.0 | 98.2 |
| 12.1 | 8.9 |
| 12.9 | 9.5 |
| 13.7 | 19.1 |
| 14.5 | 13.0 |
| 16.0 | 11.4 |
| 16.5 | 70.7 |
| 17.0 | 100.0 |
| 17.7 | 22.2 |
| 19.5 | 24.3 |
| 20.0 | 68.3 |
| 20.4 | 10.1 |
| 21.9 | 20.0 |
| 23.2 | 14.6 |
| 23.8 | 30.6 |
| 24.2 | 9.8 |
| 25.5 | 43.8 |
| 26.0 | 12.7 |
| 27.3 | 13.7 |
| 27.7 | 15.4 |
| 30.2 | 20.1 |
| 30.3 | 22.1 |
| 31.7 | 10.6 |
| 34.2 | 14.4 |
| 34.6 | 12.1 |

Example 3

(4aS,4bR,5S,6aS,6bS,8R,9aR,10aS,10bS,12S)-4b, 12-Difluoro-6b-glycoloyl-5-hydroxy-8-(4-{[(4-hydroxyphenyl)thio]methyl}phenyl)-4a 0.6a-dimethyl-4a,4b,5,6,6a,6b,9a,10,10a,10b,11,12-dodecahydro-2H-naphtho[2',1':4,5]indeno[1,2-d][1,3]dioxol-2-one

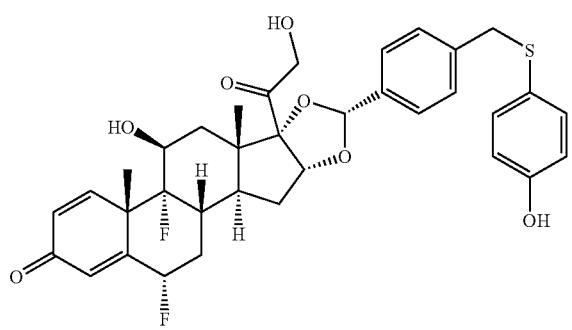

A suspension of (6α, 11β,16α)-6,9-difluoro-11,16,17,21-tetrahydroxypregna-1,4-diene-3,20-dione as obtained in Preparation 1 (99.8 mg, 0.24 mmol) and 4-{[(4-hydroxyphenyl)thio]methyl}benzaldehyde as obtained in Preparation 4 (148 mg, 0.61 mmol) in 1,4-dioxane (3 mL) was treated with dried magnesium sulphate (430 mg, 3.57 mmol) and trifluoromethanesulphonic acid (43 µL, 0.49 mmol). After stirring for one day the reaction mixture was filtered and the solid collected was washed with ethyl acetate (20 mL). The combined filtrates were poured into water (100 mL) and extracted with ethyl acetate (3-fold 20 mL). The combined organic extracts were washed with brine (50 mL) and dried (sodium sulphate) and the solvent removed in vacuo. The crude material was purified by flash column chromatography on silica gel eluting with heptane:ethyl acetate (3:1 changing to 0:1, by volume) to give the title compound as a white solid, 14% yield, 21 mg.

$^1$H NMR (400 MHz, DMSO-d$_6$) δ: 0.85 (s, 3H), 1.48 (s, 3H), 1.5 (m, 1H), 1.62-1.73 (m, 3H), 2.01-2.05 (m, 1H), 2.17-2.24 (m, 1H), 2.25-2.31 (m, 1H), 2.55-2.70 (m, 1H), 4.01 (s, 2H), 4.15-4.22 (m, 2H), 4.50 (dd, 1H), 4.94 (d, 1H), 5.05 (t, 1H), 5.43 (s, 2H), 5.48 (m, 1H), 5.55-5.71 (m, 1H), 6.11 (s, 1H), 6.28 (dd, 1H), 6.66 (d, 2H), 7.13 (d, 2H), 7.24 (m, 3H), 7.31 (d, 2H), 9.48 (s, 1H) ppm.

LRMS (ESI): m/z 639 [M+H]$^+$

Example 4

(4aS,4bR,5S,6aS,6bS,8R,9aR,10aS,10bS,12S)-4b, 12-difluoro-6b-glycoloyl-5-hydroxy-4a,6a-dimethyl-8-(4-{[3-(methylsulfinyl)phenyl]thio}phenyl)-4a,4b, 5,6,6a,6b,9a,10,10a,10b,11,12-dodecahydro-2H-naphtho[2',1':4.5]indeno[1,2-d][1,3]dioxol-2-one

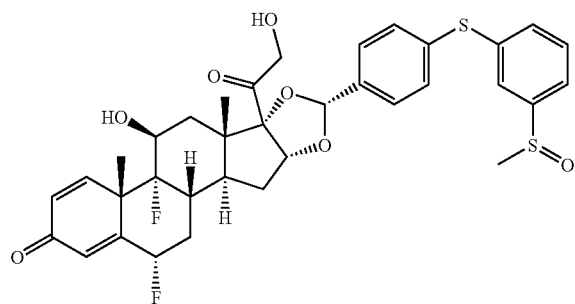

(4aS,4bR,5S,6aS,6bS,8R,9aR,10aS,10bS,12S)-4b, 12-Difluoro-6b-glycoloyl-5

5-hydroxy-4a,6a-dimethyl-8-(4-{[3-(methylthio)phenyl]thio}phenyl)-4a,4b,5,6,6a,6b,9a,10,10a,10b,11,12-dodecahydro-2Hnaphtho[2',1':4,5]-indeno[1,2-d][1,3]dioxol-2-one as prepared in Example 2 (979 mg, 1.50 mmol) was suspended in hexafluoroisopropanol (6 mL, 57.0 mmol) and cooled in an ice-bath before the dropwise addition of hydrogen peroxide (30% weight in water, 203 mg, 1.79 mmol). The reaction was stirred at ambient temperature for 90 minutes. The reaction mixture was then poured into a 25% w/v aqueous solution of sodium sulphite (30 mL). The aqueous layer was extracted with ethyl acetate (3-fold 50 mL) and the combined organic extracts were dried (sodium sulphate) and the solvent removed in vacuo. The crude material was purified by flash column chromatography on silica gel eluting with dichloromethane:methanol (9:1 by volume) to give the title compound as a white solid, 61% yield, 610 mg.

$^1$H NMR (400 MHz, DMSO-d6) δ: 0.87 (s, 3H), 1.50 (s, 3H), 1.47-1.59 (m, 1H), 1.65-1.78 (m, 3H), 2.01-2.09 (m, 1H), 2.17-2.34 (m, 2H), 2.58-2.71 (m, 1H), 2.74 (m, 3H), 4.18-4.26 (m, 2H), 4.52-4.58 (m, 1H), 4.98 (d, 1H), 5.10-5.13 (m, 1H), 5.52 (s, 1H), 5.53-5.54 (m, 1H), 5.58-5.78 (m, 1H), 6.12 (s, 1H), 6.31 (dd, 1H), 7.27 (d, 1H), 7.41-7.48 (m, 5H), 7.54-7.64 (m, 3H) ppm.

LRMS (ESI): m/z 671 [M+H]$^+$

Example 5

(4aS,4bR,5S,6aS,6bS,8R,9aR,10aS,10bS,12S)-8-(4-{[(3-chloro-4-hydroxyphenyl)thio]methyl}phenyl)-4-b,12-difluoro-6b-glycoloyl-5-hydroxy-4a,6a-dimethyl-4a,4b,5,6,6a,6b,9a,10,10a,10b. 11,12-dodecahydro-2H-naphtho[2',1':4.5]indeno[1,2-d][1.3]dioxol-2-one

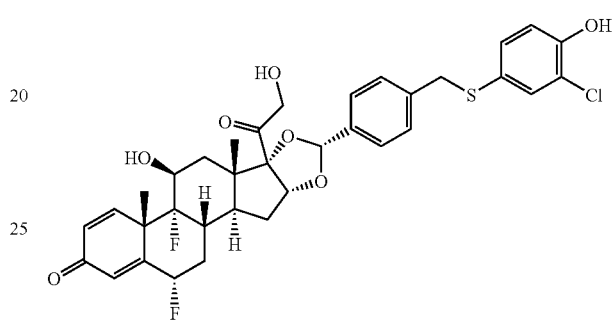

Trifluoromethanesulfonic acid (4.76 mL, 53.8 mmol) was added dropwise to an ice cold suspension of 4-{[(3-chloro-4-hydroxyphenyl)thio]methyl}benzaldehyde as obtained in Preparation 7 (5.25 g, 18.8 mmol), (6α, 11β,16α)-6,9-difluoro-11,16,17,21-tetrahydroxypregna-1,4-diene-3,20-dione as obtained in Preparation 1 (7.40 g, 17.9 mmol) and magnesium sulfate (6.82 g, 53.8 mmol) in acetonitrile (80 mL) under nitrogen. The reaction mixture was stirred at 5-10° C. for 4 hours then poured onto ice water (100 mL) and extracted with ethyl acetate (3-fold 150 mL). The combined organic layers were dried (sodium sulphate) and concentrated in vacuo affording a brown foam. This was purified by flash column chromatography (silica gel) eluting with dichloromethane:methanol (100:0 changing to 90:10 by volume) to afford an orange foam. This was further purified by flash column chromatography (silica gel) eluting with dichloromethane:methanol (100:0 changing to 90:10 by volume) to afford a yellow foam (6.0 g). This was taken up in hot ethyl acetate and seeded to induce precipitation. The solid was filtered and dried affording 1.18 g pale yellow solid. The mother liquors were evaporated, re-taken up in ethyl acetate and seeded to produce a second crop of 1.46 g. This was repeated a third time to yield a final crop of 2.40 g. All three batches were combined and triturated in hot ethyl acetate, filtered and dried affording 3.5 g of pale yellow solid, 27% yield.

$^1$H NMR (400 MHz, DMSO-d$_6$) δ: 0.86 (s, 3H), 1.50 (s, 3H), 1.48-1.57 (m, 1H), 1.62-1.77 (m, 3H), 2.01-2.08 (m, 1H), 2.18-2.33 (m, 2H), 2.55-2.72 (m, 1H), 4.09 (s, 2H), 4.16-4.24 (m, 2H), 4.48-4.55 (m, 1H), 4.93-4.97 (m, 1H), 5.45 (s, 1H), 5.50-5.53 (m, 1H), 5.55-5.61 (m, 1/2H), 5.68-5.74 (m, 1/2H), 6.13 (s, 1H), 6.27-6.32 (m, 1H), 6.85-6.88 (s, 1H), 7.10-7.13 (m, 1H), 7.25-7.36 (m, 1H), 10.28 (bs, 1H).

LRMS (ESI): m/z 673 [M]

Figure 5:
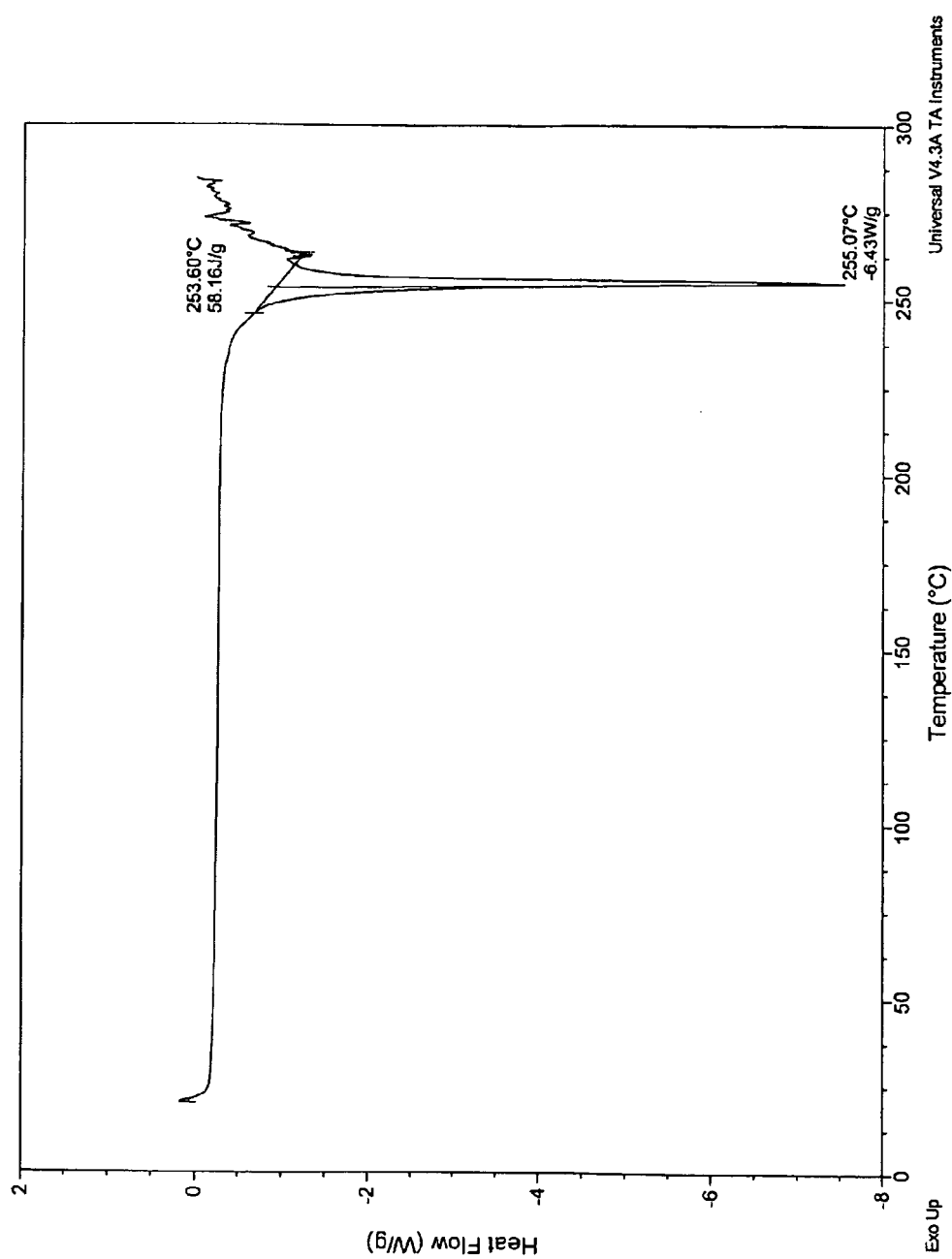

A sample of 2.769 mg was analysed by differential scanning calorimetry (DSC) with a ramp from 10° C. to 300° C. at 20° C./min. The DSC thermogram obtained is shown in FIG. 5 with a flat baseline and a sharp endotherm corresponding to the melt, peaking at 255° C.

Figure 6:
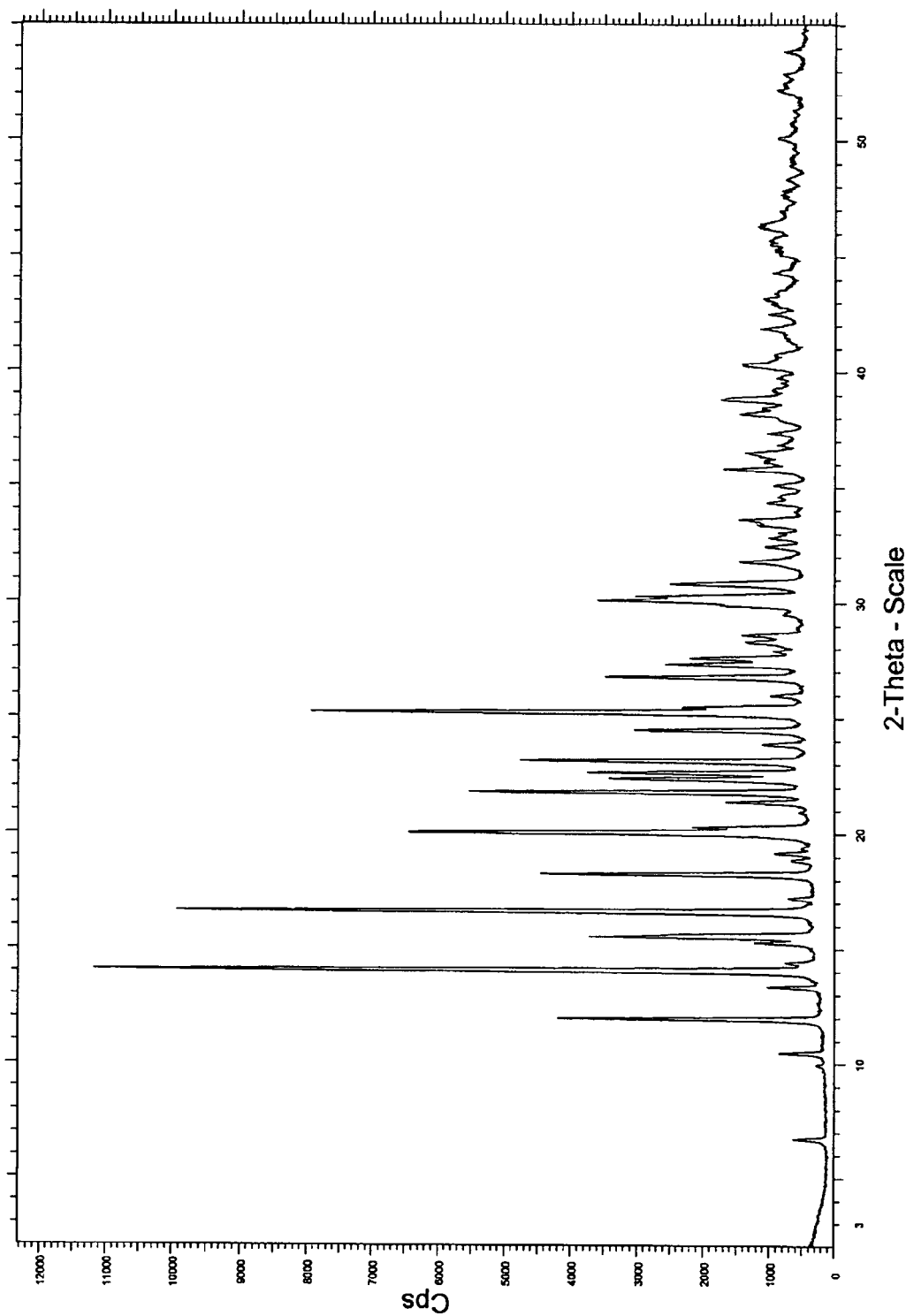

The crystalline form produced by the process described above also has the characteristics shown in the corresponding Powder X-ray diffraction pattern of FIG. 6. The main characteristic peaks are at 14.1, 16.6, 20.0, 21.8 and 25.2 degrees 2-theta±0.1 degrees 2-theta and are further given in table 3 below.

TABLE 3

Characteristic PXRD peaks for Example 5

| Angle 2-Theta (°±0.1) | Intensity (%) |
|---|---|
| 11.9 | 37.4 |
| 14.1 | 100.0 |
| 15.3 | 10.8 |
| 15.5 | 32.0 |
| 16.6 | 88.7 |
| 18.3 | 39.5 |
| 20.0 | 57.6 |
| 20.3 | 18.8 |
| 21.4 | 14.5 |
| 21.8 | 49.3 |
| 22.4 | 30.4 |
| 22.6 | 33.1 |
| 23.1 | 42.4 |
| 24.5 | 27.0 |
| 25.2 | 70.8 |
| 25.4 | 20.1 |
| 26.8 | 30.8 |
| 27.3 | 22.9 |
| 27.6 | 19.4 |
| 28.3 | 12.0 |
| 28.6 | 12.2 |
| 29.9 | 15.4 |
| 30.1 | 31.9 |
| 30.3 | 26.4 |
| 30.8 | 22.1 |
| 31.8 | 12.9 |
| 33.4 | 10.3 |
| 33.6 | 12.2 |
| 35.8 | 15.1 |
| 36.5 | 11.7 |
| 38.2 | 12.9 |
| 38.9 | 15.4 |
| 40.3 | 12.4 |

Example 6

In Vitro Pharmacological Activity

The pharmacological activity of the compounds of formula (I) was assessed in in vitro assays of glucocorticoid agonist activity and in human blood and isolated leukocyte TNF-α release assays which are predictive of anti-inflammatory activity in vivo.

Glucocorticoid receptor (GR) agonist potency was determined in the human chondrosarcoma cell-line SW1353 stably transfected with an MMTV-luciferase reporter construct. SW1353 naturally expresses human GR, which on binding a glucocorticoid agonist activates glucocorticoid response elements within the MMTV promoter, driving expression of the luciferase gene.

Frozen SW1353 cells were revived in DMEM medium, without sodium pyruvate or phenol red, supplemented with 2 mM L-glutamine, 1 µg/ml insulin, 2 mg/ml lactalbumin hydroxylate and 0.5 µg/ml ascorbate. Cells were seeded at approximately 5000 cells/well (35 µl/well) in 384-well clear bottom, tissue culture treated plates. Steroid dose-response dilutions were prepared in steroid diluent (PBS containing 2.5% (v/v) DMSO and 0.05% (v/v) pluronic detergent) and 5 µl added to each well. The volume was made up to 50 µl per well with steroid diluent. Positive control wells contained 1 µM dexamethasone. Plates were incubated for approximately 18 hours at 37° C. in an air/5% $CO_2$ atmosphere in a humidified incubator before Britelite reagent (10 µl; Perkin-Elmer) was added to each well. Each plate was incubated for 2 minutes in the dark and luminescence quantified using a LJL Biosystems Analyst luminometer. Data for test compounds (expressed as percentage of the dexamethasone positive control) were used to construct dose response curves from which $EC_{50}$ values were estimated. The following data have been obtained:

| Example No. | GR agonist $EC_{50}$ (nM) |
|---|---|
| 1 | 0.75 |
| 2 | 5.0 |
| 3 | 1.7 |
| 4 | 0.5 |
| 5 | 9.84 |

The anti-inflammatory activity of the compounds against human leukocytes in vitro was also evaluated by determining inhibition of tumour necrosis factor-α (TNF-α) release from lipopolysaccharide (LPS) stimulated human whole blood (WB) and isolated human peripheral mononuclear cells (PBMC).

Peripheral venous blood from healthy, non-medicated donors was collected using ethylenediaminetetraacetic acid (EDTA) as the anti-coagulant. For PBMC preparation, samples of blood were diluted 1:1 with sterile phosphate buffered saline and then separated using ACCUSPIN™ System-Histopaque®-1077 tubes (Sigma-Aldrich, St Louis, Mo.), centrifuged at 400 g for 35 minutes. Buffy coat cells were removed into PBS, centrifuged at 200 g for 10 minutes and re-suspended in PBMC assay buffer (Hanks Balanced Salt Solution, 0.28% [w/v] 4-[2-hydroxyethyl]-1-piperazineethanesulfonic acid [HEPES], 0.01% [w/v] low-endotoxin bovine serum albumin [BSA]. A differential white cell count was performed and PBMC's diluted to $1 \times 10^6$ lymphocytes per ml in PBMC assay buffer.

Test compounds were dissolved in DMSO and diluted in PBMC assay buffer (final DMSO concentration 1%) to cover an appropriate concentration range, e.g 0.001 nM to 10000 nM. Samples of test compound solution or vehicle (20 µl) were added into 96-well tissue culture treated plates (Corning) and PBMC (160 µl) or WB (160 µl) added to each well. The assay mixtures were incubated at 37° C. for 1 h in a humidified incubator containing an atmosphere of air supplemented with 5% $CO_2$ before adding LPS (20 µl of 100 ng/ml for PBMC or 1 µg/ml for WB). Plates were returned to the incubator for a further 18 hours, and then centrifuged before recovery of samples of supernatant. TNF-α in the samples was determined using an enzyme-linked immunosorbent assay (ELISA) (Invitrogen kit no CHC-1754; Invitrogen Carlsbad, Calif.) and following the manufacturers instructions. Dose response curves were constructed from which $IC_{50}$ values were calculated. The following data have been obtained:

| Example No. | IC$_{50}$ (nM) for inhibition of TNF-α release | |
|---|---|---|
| | PBMC | Whole Blood |
| 1 | 0.098 | 17 |
| 2 | 0.092 | 49 |
| 3 | 0.061 | 24 |
| 4 | 0.059 | 40 |
| 5 | 0.032 | 8.73 |

Example 7

In Vivo Pharmacological Activity

The pharmacological activity may be assessed in in vivo models of lung inflammation such as the one described below. The primary objective of this procedure was to determine the anti-inflammatory activity of the compounds of formula (I), when administered directly into the lungs via the trachea.

Test compounds were dissolved, or prepared as fine suspensions, in phosphate buffered saline containing 0.5% (w/v) Tween-80 to provide a range of dose levels. Male CD Sprague-Dawley rats (300-450 g) were randomised to study groups of n=6 and then briefly anaesthetised in an anaesthetic chamber with 5% Isoflurane in 3 l/min $O_2$. One of the test compound formulations or dose vehicle (100 μl) was injected directly into the trachea of each anaesthetised rat using a Hamilton syringe. The animals were then allowed to recover from the anaesthetic. Dependent on the study design, animals received either a single dose of compound or were treated once daily on 4 successive days. Four hours after the dosing (or 4 hours after the final dose in repeat dose studies) the rats were placed into a chamber (300×300×450 mm), connected to an ultrasonic nebuliser and a small animal rodent ventilator set to the maximum tidal volume and rate (5 ml, 160 strokes/min). 10 ml of 1 mg/ml LPS (Sigma-Aldrich, L2630) dissolved in saline, pre-warmed to 37° C., was nebulised into the chamber. After 15 minutes the ventilator and nebuliser were turned off and the animals remained in the chamber to breathe the mist for a further 15 minutes before being returned to the home cage.

Four hours after the end of the LPS treatment the animals were terminally anaesthetised with 1 ml/kg Pentoject IP. The trachea was cannulated and the lungs lavaged with 4×2.5 ml PBS containing 2.6 mM EDTA and the lavage fluid collected. 1 ml bronchioalveolar lavage (BAL) was added to 125 μl of 40% bovine serum albumen (BSA) and the cellular count determined using an Advia 120 haematology system (Siemens). In repeat dose studies, bodyweights and weights of adrenal glands and thymus were also determined as these are known to decrease in response to glucocorticoid agonist exposure and have been used to assess the systemic effects of glucocorticoid agonists. In some repeat dose experiments, a terminal blood sample was collected from each rat, serum and plasma prepared, and concentrations of corticosterone in serum and ACTH in plasma were determined as additional markers of systemic glucocorticoid agonist effect. In some studies a known glucocorticoid agonist, fluticasone propionate, was administered to separate groups of rats as a positive control.

Separate dose response curves were constructed, for inhibition of LPS-induced lung neutrophils, and each marker of glucocorticoid agonist systemic effect. Half maximal effect doses ($ED_{50}$) values were estimated from the fitted curves.

The $ED_{50}$ values for effect on systemic markers of glucocorticoid agonist activity were also divided by the $ED_{50}$ for inhibition of lung neutrophilia in order to determine values for therapeutic index (TI).

It has thus been found that compounds of formula (I) according to the present invention that have been tested in the above assay show activity for inhibition of lung neutrophilia after administration of a single dose as listed in the table below:

| Example No. | $ED_{50}$ (μg) |
|---|---|
| 1 | 0.27 |
| 2 | 0.18 |
| 3 | 0.45 |
| 4 | 2.00 |
| 5 | 3.6 |

The invention claimed is:
1. A compound of formula (I):

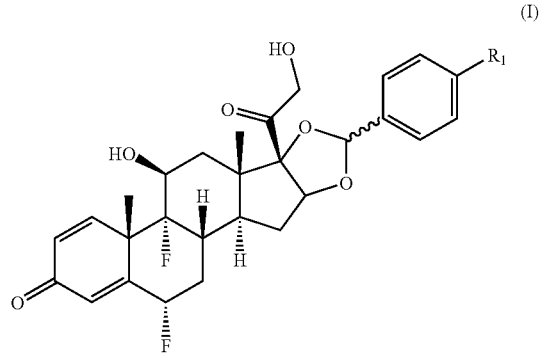

(I)

wherein $R_1$ is selected from the group consisting of:

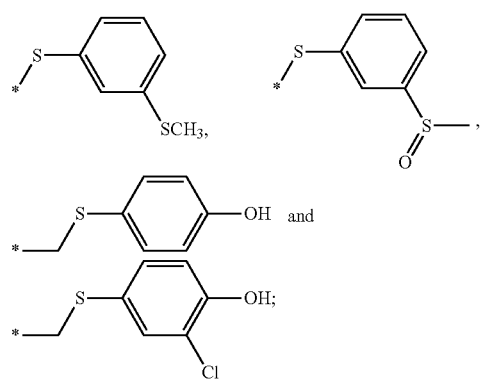

wherein * represent the attachment point of $R_1$ to the carbon of the phenyl cycle;
or a pharmaceutically acceptable salt thereof or a pharmaceutically acceptable solvate of said compound or salt.
2. The compound of claim 1, or a pharmaceutically acceptable salt thereof or a pharmaceutically acceptable solvate of said compound or salt, selected from the group consisting of:
(4aS,4bR,5 S,6aS,6bS,8R,9aR,10aS,10bS,12S)-4b,12-difluoro-6b-glycoloyl-5-hydroxy-4a,6a-dimethyl-8-(4-{[3-(methylthio)phenyl]thio}phenyl)-4a,4b,5,6,6a,6b, 9a,10,10a,10b,11,12-dodecahydro-2H-naphtho[2',1':4,5]indeno[1,2-d][1,3]dioxol-2-one;

(4aS,4bR,5S,6aS,6bS,8R,9aR,10aS,10bS,12S)-4b,12-difluoro-6b-glycoloyl-5-hydroxy-8-(4-{[(4-hydroxyphenyl)thio]methyl}phenyl)-4a,6a-dimethyl-4a,4b,5,6,6a,6b,9a,10,10a,10b,11,12-dodecahydro-2H-naphtho[2',1':4,5]indeno[1,2-d][1,3]dioxol-2-one;

(4aS,4bR,5S,6aS,6bS,8R,9aR,10aS,10bS,12S)-4b,12-difluoro-6b-glycoloyl-5-hydroxy-4a,6a-dimethyl-8-(4-{[3-(methylsulfinyl)phenyl]thio}phenyl)-4a,4b,5,6,6a,6b,9a,10,10a,10b,11,12-dodecahydro-2H-naphtho-[2',1':4,5]indeno[1,2-d][1,3]dioxol-2-one; and (4aS,4bR,5S,6aS,6bS,8R,9aR,10aS,10bS,12S)-8-(4-{[(3-chloro-4-hydroxyphenyl)thio]methyl}phenyl)-4b,12-difluoro-6b-glycoloyl-5-hydroxy-4a,6a-dimethyl-4a,4b,5,6,6a,6b,9a,10,10a,10b,11,12-dodecahydro-2H-naphtho[2',1':4,5]indeno[1,2-d][1,3]dioxol-2-one.

3. The compound of claim 1, or a pharmaceutically acceptable salt thereof, which is (4aS,4bR,5S,6aS,6bS,8R,9aR,10aS,10bS,12S)-4b,12-difluoro-6b-glycoloyl-5-hydroxy-4a,6a-dimethyl-8-(4-{[3-(methylthio)phenyl]thio}phenyl)-4a,4b,5,6,6a,6b,9a,10,10a,10b,11,12-dodecahydro-2H-naphtho[2',1':4,5]indeno[1,2-d][1,3]dioxol-2-one.

4. The compound of claim 1, or a pharmaceutically acceptable salt thereof, which is (4aS,4bR,5S,6aS,6bS,8R,9aR,10aS,10bS,12S)-8-(4-{[(3-chloro-4-hydroxyphenyl)thio]methyl}phenyl)-4b,12-difluoro-6b-glycoloyl-5-hydroxy-4a,6a-dimethyl-4a,4b,5,6,6a,6b,9a,10,10a,10b,11,12-dodecahydro-2H-naphtho[2',1':4,5]indeno[1,2-d][1,3]dioxol-2-one.

5. A pharmaceutical composition comprising an effective amount of a compound of the formula (I) as described in any one of claim 1, or a pharmaceutically acceptable salt thereof, and a pharmaceutically acceptable excipient.

* * * * *